United States Patent
North et al.

(10) Patent No.: US 10,155,810 B2
(45) Date of Patent: Dec. 18, 2018

(54) PROVASOPRESSIN ANTAGONISTS AND USES THEREOF

(71) Applicant: Woomera Therapeutics, Inc., Lebanon, NH (US)

(72) Inventors: William G. North, Hanover, NH (US); Roy H. L. Pang, Etna, NH (US)

(73) Assignee: Woomera Therapeutics, Lebanon, NH (US)

( * ) Notice: Subject to any disclaimer, the term of this patent is extended or adjusted under 35 U.S.C. 154(b) by 0 days.

(21) Appl. No.: 15/289,260

(22) Filed: Oct. 10, 2016

(65) Prior Publication Data
US 2017/0107283 A1    Apr. 20, 2017

Related U.S. Application Data

(63) Continuation of application No. 14/274,997, filed on May 12, 2014, which is a continuation of application No. PCT/US2012/064336, filed on Nov. 9, 2012.

(60) Provisional application No. 61/558,998, filed on Nov. 11, 2011.

(51) Int. Cl.
| | |
|---|---|
| A61K 39/395 | (2006.01) |
| C07K 16/26 | (2006.01) |
| A61K 31/137 | (2006.01) |
| A61K 38/10 | (2006.01) |
| A61K 45/06 | (2006.01) |
| A61K 47/48 | (2006.01) |
| A61K 49/00 | (2006.01) |
| A61K 51/10 | (2006.01) |
| G01N 33/574 | (2006.01) |
| C07K 16/30 | (2006.01) |
| A61K 39/00 | (2006.01) |

(52) U.S. Cl.
CPC ............ *C07K 16/26* (2013.01); *A61K 31/137* (2013.01); *A61K 38/10* (2013.01); *A61K 39/39558* (2013.01); *A61K 45/06* (2013.01); *A61K 47/48553* (2013.01); *A61K 49/00* (2013.01); *A61K 51/1024* (2013.01); *C07K 16/303* (2013.01); *C07K 16/3015* (2013.01); *C07K 16/3023* (2013.01); *C07K 16/3069* (2013.01); *G01N 33/57415* (2013.01); *G01N 33/57423* (2013.01); *A61K 2039/505* (2013.01); *C07K 2317/21* (2013.01); *C07K 2317/24* (2013.01); *C07K 2317/55* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,807,397 B2 * | 10/2010 | Bergmann | G01N 33/74 422/430 |
| 2008/0050376 A1 | 2/2008 | North et al. | |
| 2008/0267963 A1 * | 10/2008 | Kislauskis | A61K 39/0011 424/138.1 |
| 2010/0041064 A1 | 2/2010 | Bergmann et al. | |
| 2011/0008911 A1 | 1/2011 | Bergmann et al. | |
| 2014/0341802 A1 | 11/2014 | North et al. | |

FOREIGN PATENT DOCUMENTS

| | | |
|---|---|---|
| EP | 0399257 A1 | 11/1990 |
| EP | 1628136 A1 | 2/2006 |
| WO | WO 2009/137113 | * 11/2009 |

OTHER PUBLICATIONS

Dimopoulos et al (J Urology, 2004, 63:120-125).*
Mitsiades et al (Anticancer Research, 2006, 26:3693-3700).*
Hwang et al (J of Hematology, 2010, 3:26, internet pp. 1-12).*
Zimmerman et al (Drug Discovery Today, Jan. 2007, 12: 34-42).*
Dahut et al (J Clinical Oncology, 2004, 22:2532-2539).*
Fehn et al (Exp, Clin. Endocrinol. Diabetes, 1998, 106:425-430).*
North et al (Experimental Physiology, 2000, 85S: 27S-40S) in IDS.*
Bamberger et al., The Neuro-2a neuroblastoma cell line expresses [Met]-enkephalin and vasopressin mRNA and peptide. Mol Cell Endocrinol. Sep. 22, 1995;113(2)155-63.
Biete et al., Whole abdominal radiotherapy in ovarian cancer. Rep Pract Oncol Radiother. Mar. 23, 2010;15(2):27-30.
Gruson et al., Laboratory medicine: the precursors strike back. Acta Clin Belg. May-Jun. 2011;66(3):216-20.
Keegan et al., Detection of Provasopressin in Invasive and Non-invasive (DCIS) Human Breast Cancer Using a Monoclonal Antibody Directed Against the C-terminus (MAG1). Breast Cancer (Auckl). Apr. 8, 2010;4:15-22.
Keegan et al., Provasopressin expression by breast cancer cells: implications for growth and novel treatment strategies. Breast Cancer Res Treat. Feb. 2006;95(3):265-77.

(Continued)

*Primary Examiner* — Laura B Goddard

(74) *Attorney, Agent, or Firm* — McCarter & English, LLP; Elizabeth A. Hanley; Yu Lu

(57) ABSTRACT

Provided herein are pro-VP antagonists, such as antibodies and antigen-binding portions thereof specific for pro-VP, for identifying and targeting expressing cancer cells. Applicants additionally provide methods of using said compositions, for example to image cancer cells in vivo and in biological samples. The compositions may also be used for treating patients suffering from a provasopressin-expressing cancer. Provasopressin-expressing cancers include neuroendocrine cancer, pancreatic cancer, and prostate cancer.

18 Claims, 13 Drawing Sheets

Specification includes a Sequence Listing.

(56) References Cited

OTHER PUBLICATIONS

North et al., Immunohistochemical evaluation of vasopressin expression in breast fibrocystic disease and ductal carcinoma in situ (DCIS). Endocr Pathol. 2003 Fall;14(3):257-62.
North, Gene regulation of vasopressin and vasopressin receptors in cancer. Exp Physiol. Mar. 2000;85 Spec No. 27S-40S.
Woll et al., A neuropeptide antagonist that inhibits the growth of small cell lung cancer in vitro. Cancer Res. Jul. 1, 1990;50(13)3968-73.

* cited by examiner

NCI-H82

FIG. 3A
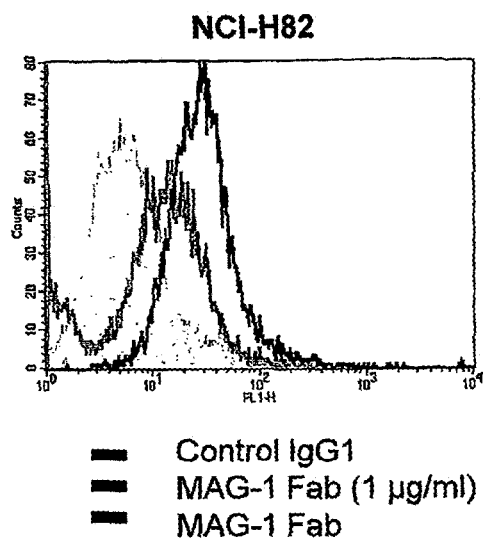
- Control IgG1
- MAG-1 Fab (1 µg/ml)
- MAG-1 Fab
FIG. 3B
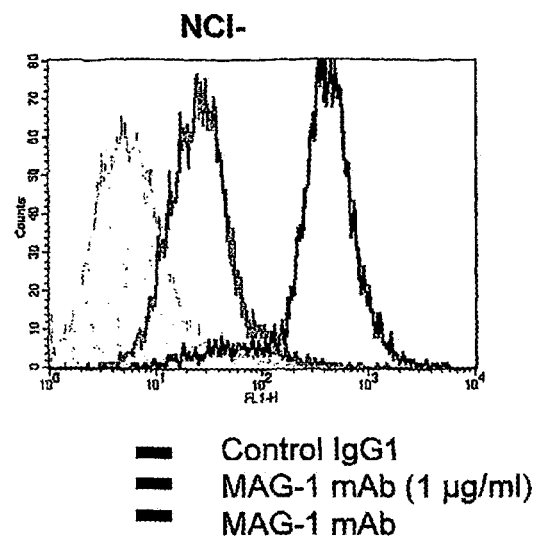
- Control IgG1
- MAG-1 mAb (1 µg/ml)
- MAG-1 mAb
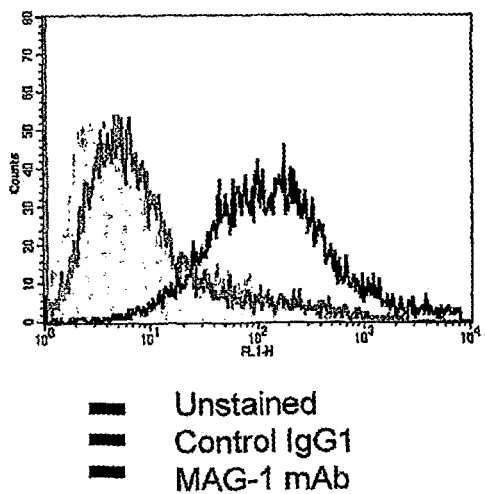
- Unstained
- Control IgG1
- MAG-1 mAb
FIG. 3C
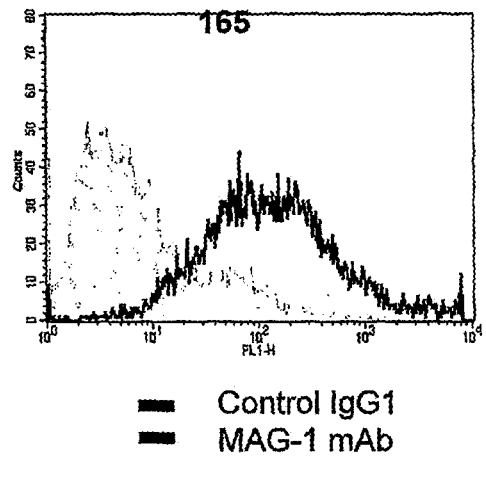
- Control IgG1
- MAG-1 mAb
FIG. 3D FIG. 4A
NCI-H82
MAG-1
+
Propidium
Iodide
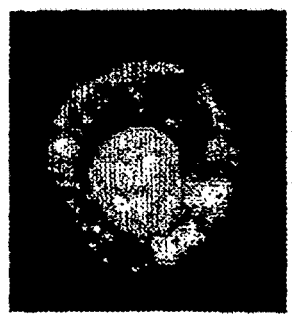
FIG. 4B
NCI-H345
Control
IgG1
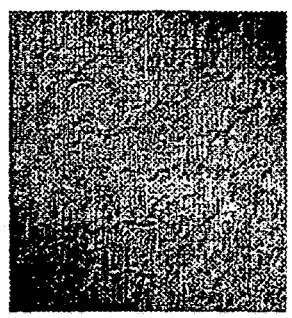  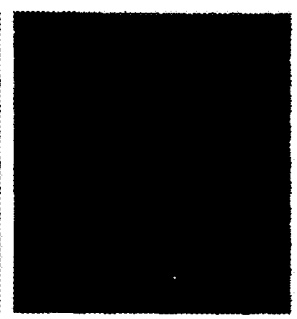
MAG-1
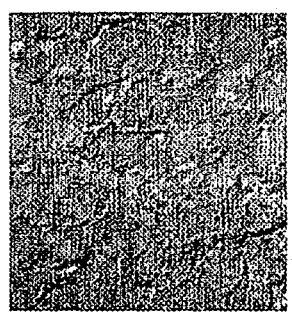 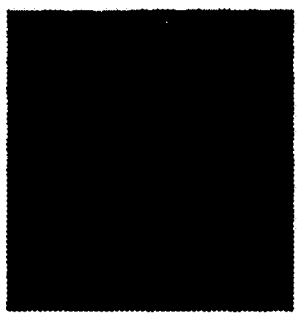 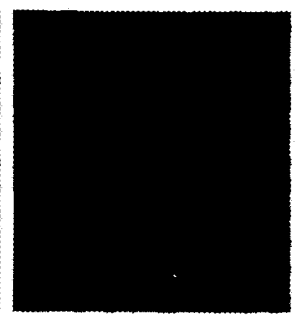
FIG. 4C
Lu-165
Control
IgG1
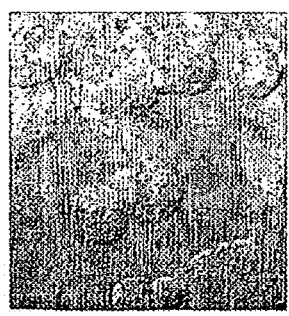  
MAG-1
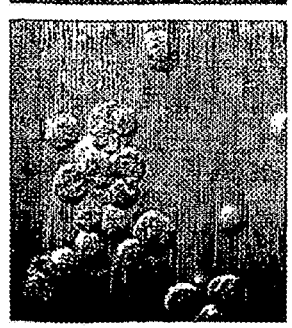  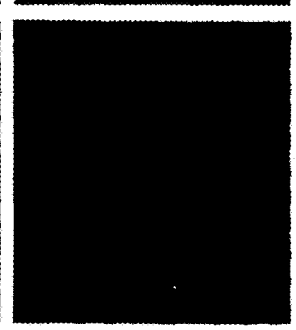

FIG. 6A

MKKTAIAIAVALAGFATVAQAEVKLXESGGGLVHPGGSMKLSCVASGFTFS
NYWMNWVRQSPEKGLEWVAEIRLKSNNYATHYAESVKARFTISRDDSKST
VYLQMNNLRGEDTGIYYCTRDVGRDYWGHGSTLTVSGSTSGDIVMTPTPLS
LSVTIGQPASISCKSSQSLLYSNGKTYLNWLQQRPGQAPKHLMYQVSKLDP
GIPDRFSGSGSKTDFTLXISRXEAEDWXVYYCFQGHIIRTRTGXPAGRAX
(SEQ ID NO: 2)

FIG. 6B

ATGAAAAAGACAGCTATCGCGATTGCAGTGGCACTGGCTGGTTTCGCTA
CCGTAGCGCAGGCCGAGGTCAAGCTGCNTGAGTCAGGAGGAGGCTTGGT
GCATCCTGGAGGATCCATGAAACTCTCCTGTGTTGCCTCTGGATTCACTT
TCAGTAACTACTGGATGAACTGGGTCCGCCAGTCTCCAGAGAAGGGGCT
TGAGTGGGTTGCTGAAATTAGATTGAAATCTAATAATTATGCAACACATT
ATGCGGAGTCTGTGAAAGCGAGGTTCACCATCTCAAGAGATGATTCCAA
AAGTACTGTCTACCTGCAAATGAACAACTTAAGAGGTGAAGACACTGGC
ATTTATTACTGTACCAGGGACGTGGGACGTGACTACTGGGGCCATGGCT
CCACTCTCACAGTCTCCGGCTCTACTTCCGGTGATATCGTTATGACCCCA
ACTCCACTCTCTTTGTCGGTACCATTGGACAACCAGCCTCTATCTCTTGC
AAGTCAAGTCAGAGCCTCTTATATAGTAATGGAAAGACATATTTGAATT
GGTTACAACAGAGGCCTGGCCAGGCTCCAAAGCACCTAATGTATCAGGT
GTCCAAACTGGACCCTGGCATCCCTGACAGGTTCAGTGGCAGTGGATCA
AAAACAGATTTTACACCTNAAATCAGCAGAGNGGAGGCTGAAGATTGGG
NAGTTTATTACTGCTTCCAGGGACATATAATCCGTACTCGTACGGGCCCN
CCAGCTGGAAGGGCANNC (SEQ ID NO: 3)

Breast Cancer

Ovarian Cancer

FIG. 13A
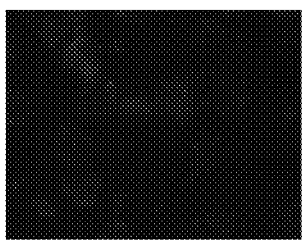
SKOV3
FIG. 13B
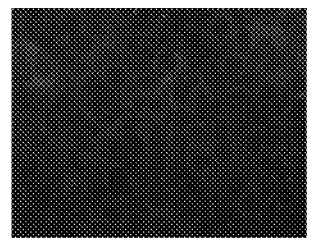
bxpc3
FIG. 13C
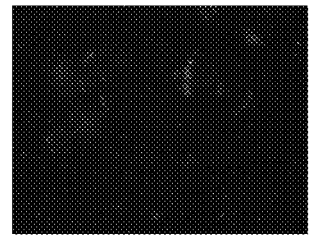
PC3
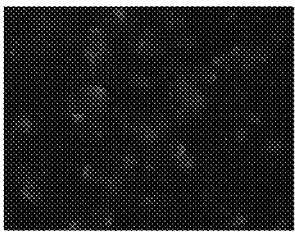
OV2008
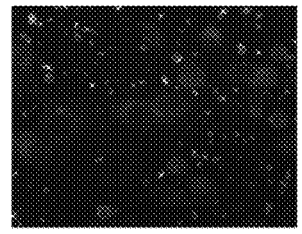
panc1
FIG. 13D      FIG. 13E

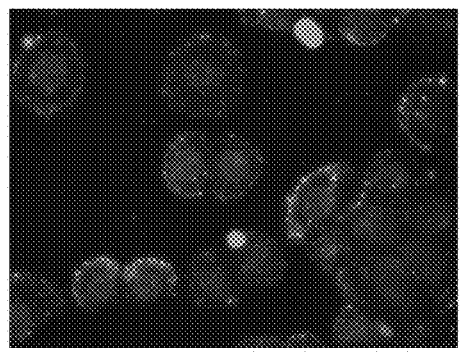 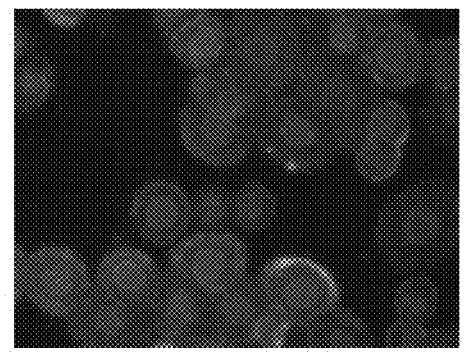
FIG. 16A    FIG. 16B
FIG. 17
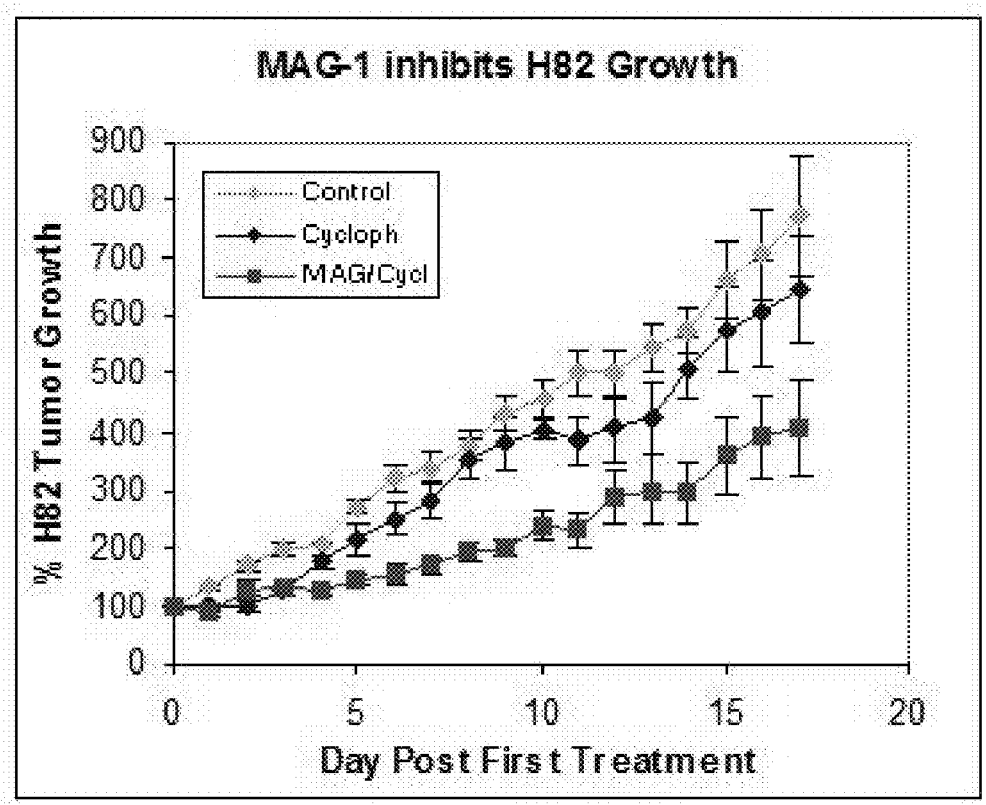

SEQUENCE LISTING

<160> NUMBER OF SEQ ID NOS: 21

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ala Pro Glu Pro Phe Glu Pro Ala
1               5

<210> SEQ ID NO 2
<211> LENGTH: 253
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (231)..(231)
<223> OTHER INFORMATION: Xaa can be any naturally occurring amino acid
<220> FEATURE:
<221> NAME/KEY: misc_feature
<222> LOCATION: (247)..(247)
<223> OTHER INFORMATION: Xaa can be any naturally occurring amino acid
<220> FEATURE:
<221> NAME/KEY: misc_feature
<222> LOCATION: (253)..(253)
<223> OTHER INFORMATION: Xaa can be any naturally occurring amino acid

<400> SEQUENCE: 2

Met Lys Lys Thr Ala Ile Ala Ile Ala Val Ala Leu Ala Gly Phe Ala
1               5                   10                  15

Thr Val Ala Gln Ala Glu Val Lys Leu Xaa Glu Ser Gly Gly Gly Leu
                20                  25                  30

Val His Pro Gly Gly Ser Met Lys Leu Ser Cys Val Ala Ser Gly Phe
            35                  40                  45

Thr Phe Ser Asn Tyr Trp Met Asn Trp Val Arg Gln Ser Pro Glu Lys
        50                  55                  60

Gly Leu Glu Trp Val Ala Glu Ile Arg Leu Lys Ser Asn Asn Tyr Ala
65                  70                  75                  80

Thr His Tyr Ala Glu Ser Val Lys Ala Arg Phe Thr Ile Ser Arg Asp
                85                  90                  95

Asp Ser Lys Ser Thr Val Tyr Leu Gln Met Asn Asn Leu Arg Gly Glu
            100                 105                 110

```
Asp Thr Gly Ile Tyr Tyr Cys Thr Arg Asp Val Gly Asp Tyr Trp
            115                 120                 125

Gly His Gly Ser Thr Leu Thr Val Ser Gly Ser Thr Gly Asp Ile
130                 135                 140

Val Met Thr Pro Thr Pro Leu Ser Leu Ser Val Thr Ile Gly Gln Pro
145                 150                 155                 160

Ala Ser Ile Ser Cys Lys Ser Ser Gln Ser Leu Leu Tyr Ser Asn Gly
                165                 170                 175

Lys Thr Tyr Leu Asn Trp Leu Gln Gln Arg Pro Gly Gln Ala Pro Lys
            180                 185                 190

His Leu Met Tyr Gln Val Ser Lys Leu Asp Pro Gly Ile Pro Asp Arg
        195                 200                 205

Phe Ser Gly Ser Gly Ser Lys Thr Asp Phe Thr Leu Xaa Ile Ser Arg
210                 215                 220

Xaa Glu Ala Glu Asp Trp Xaa Val Tyr Tyr Cys Phe Gln Gly His Ile
225                 230                 235                 240

Ile Arg Thr Arg Thr Gly Xaa Pro Ala Gly Arg Ala Xaa
            245                 250
```

<210> SEQ ID NO 3
<211> LENGTH: 759
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (77)..(77)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t
<220> FEATURE:
<221> NAME/KEY: misc_feature
<222> LOCATION: (674)..(674)
<223> OTHER INFORMATION: n is a, c, g, or t
<220> FEATURE:
<221> NAME/KEY: misc_feature
<222> LOCATION: (692)..(692)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (757)..(758)
<223> OTHER INFORMATION: n is a, c, g, or t

<400> SEQUENCE: 3

```
atgaaaaaga cagctatcgc gattgcagtg gcactggctg gtttcgctac cgtagcgcag      60
gccgaggtca agctgcntga gtcaggagga ggcttggtgc atcctggagg atccatgaaa     120
ctctcctgtg ttgcctctgg attcactttc agtaactact ggatgaactg ggtccgccag     180
tctccagaga agggcttga gtgggttgct gaaattagat tgaaatctaa taattatgca      240
acacattatg cggagtctgt gaaagcgagg ttcaccatct caagagatga ttccaaaagt     300
actgtctacc tgcaaatgaa caacttaaga ggtgaagaca ctggcattta ttactgtacc     360
agggacgtgg gacgtgacta ctggggccat ggctccactc tcacagtctc cggctctact     420
tccggtgata tcgttatgac cccaactcca ctctctttgt cggttaccat tggacaacca     480
gcctctatct cttgcaagtc aagtcagagc ctcttatata gtaatggaaa gacatatttg     540
```

```
aattggttac aacagaggcc tggccaggct ccaaagcacc taatgtatca ggtgtccaaa      600
ctggaccctg gcatccctga caggttcagt ggcagtggat caaaaacaga ttttacacct      660
naaatcagca gagnggaggc tgaagattgg gnagtttatt actgcttcca gggacatata      720
atccgtactc gtacgggccc nccagctgga agggcannc                             759
```

```
<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Gly Gly Ser Ser Arg Ser Ser
1               5

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Val Gln Leu Ala Gly Ala Pro Glu Pro Phe Glu Pro Ala Gln Pro Asp
1               5                   10                  15

Ala Tyr

<210> SEQ ID NO 6
<211> LENGTH: 10
<212> TYPE: PRT
<213> ORGANISM: Artificial Sequence
<220> FEATURE:
<223> OTHER INFORMATION: Synthetic peptide

<400> SEQUENCE: 6

Val Gln Leu Ala Gly Ala Pro Glu Pro Phe
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Gly Ser Thr Ser Gly
1               5

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
aggatgcctg acaccatgct g                                                 21

<210> SEQ ID NO 9
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 9
attggcggag gtttattgtc                                                    20

<210> SEQ ID NO 10
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 10
gggcccaggc ggccgagctc gayatccagc tgactcagcc                              40

<210> SEQ ID NO 11
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 11
cctggccggc ctggccacta gtgacagatg gggstgtygt tttgg                        45

<210> SEQ ID NO 12
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 12
ggaagatcta gaggaaccac ctttkatttc cagyttggtc cc                           42

<210> SEQ ID NO 13
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 13
ggtggttcct ctagatcttc cctcgaggtr magcttcagg agtc                         44

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
aggtsmarct gcagsagtcw gg                                                 22

<210> SEQ ID NO 15
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 15
ccaggggcca gtggatagac aagcttgggt gtcgtttt                                38
```

```
<210> SEQ ID NO 16
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 16
ggtgatatcw tgmtgaccca awctccactc tc                                    32

<210> SEQ ID NO 17
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 17
gggaagatgg atccagttgg tgcagcatca gc                                    32

<210> SEQ ID NO 18
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 18
gggcccaggc ggccgaggtc aagctgcagg agtca                                 35

<210> SEQ ID NO 19
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 19
cctggccggc ctggccttttk atttccagyt tggtccc                              37

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20
accggaagta gagccggaga ctgtgagagt ggagcc                                36

<210> SEQ ID NO 21
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 21
ggctctactt ccggtgatat cgttatgacc ccaact                                36
```

PROVASOPRESSIN ANTAGONISTS AND USES THEREOF

REFERENCE TO RELATED APPLICATIONS

This application is a continuation application of U.S. Ser. No. 14/274,997, filed on May 12, 2014, which is a continuation application of International Application No. PCT/US2012/064336, filed on Nov. 9, 2012 and designated the U.S., and was published as WO 2013/071030, which International Application claims the benefit of the filing date of U.S. Provisional Application No. 61/558,998, filed on Nov. 11, 2011, the entire contents of each of the above applications are incorporated herein by reference.

GOVERNMENT SUPPORT

The invention described herein may have been supported, in whole or in part, by the following grants from the National Institutes of Health (NIH) of the U.S. Department of Health and Human Services (USHHS): 2R44CA119483-02A1 & 5R44x119483-03. The U.S. government may have certain rights in the claimed invention.

BACKGROUND OF THE INVENTION

Ovarian cancer is the fifth leading causes of death from cancer among women throughout the world, and accounts for the death of approximately 16,000 women in the United States each year (Young, "Gynecologic Malignancies," in J. N. Jameson, D. L. Kasper, T. R. Harrison, E. Braunwald, A. S. Fauci, S. L. Hauser, D. L. Longo (eds.) *Harrison's Principles of Internal Medicine*, 16th Edition, McGraw-Hill, New York, N.Y., 2005). Although there have been many recent advances for effectively treating this disease (Goff et al., "Ovarian carcinoma diagnosis," *Cancer* 89: 2068-2075, 2000; Chobanian and Dietrich, "Ovarian Cancer," *Surg. Clin. North Amer.* 88:285-299, 2008), successful intervention still relies heavily on early detection and surgical removal. Therefore, a pressing need exists for the development of new non-surgical methods of treatment that are effective in terms of providing long-term survival for patients, and precise methods for identifying and evaluating changes in tumor burden.

Pancreatic cancer is the eighth most frequent type of solid tumor arising worldwide, but, as a consequence of the current lack of effective therapy, it is the fourth most frequent cause of cancer death (Gunzburg and Salmons, *Trends Mol. Med.* 7(1):30-37, 2001). It is estimated that 29,200 cases will be diagnosed in the United States in 2001, and 28,900 of these patients are expected to die (*Cancer Facts and Figures*, 2001. Atlanta, Ga., American Cancer Society, 2001). Long-term survival for patients with organ-confined disease is only 20 percent, and in the majority of cases, in which the disease, when diagnosed, has already spread past the pancreas, survival is only 4 percent (Hilgers and Kern, Genes, *Chromosomes & Cancer* 26: 1-12, 1999; Regine et al., *Front. Biosci.* 3: E186-E192, 1998; Blaszkowsky, *Front. Biosci.* 3:E214-E225, 1998; Lorenz et al., *Eur. J. Cancer* 36:957-965, 2000; Rosenberg, *Drugs* 59:1071-1089, 2000).

As the most common internal cancer in older men and the seventh most common cause of death in men of all ages in developed countries, cancer of the prostate is a serious health problem in terms of drawn-out personal suffering and premature death not to mention the cost to the health care system. The incidence of prostate cancer appears to be increasing, over and above improved detection rates in recent years (Post et al., 1999). Although many men with cancer of the prostate die from other causes, the high incidence results in significant morbidity and death directly from the prostatic tumor. Currently-available therapy carries a significant risk of major side effects, including incontinence and impotence, and consequently many men are reluctant to accept treatment at an early stage of the disease. The need to improve the treatment of prostate cancer is underlined by the existence of over 150 clinical trials world wide (*Future Oncology*, vol. 4, number 3, 1998).

The expression of the vasopressin gene is largely restricted to hypothalamic neurons, and it encodes for a protein product of ~17 kDa, to which an N-glycosidic side-chain of ~4 kDa is added, resulting in the ~20 kDa provasopressin (pro-VP) precursor. This protein is normally packaged into secretory vesicles where it undergoes enzymatic cleavage to generate vasopressin (VP), VP-associated neurophysin (VP-NP), and VP-associated glycopeptide (VAG) (North, W. G. In: D. Gash and G. Boer (eds.), *Vasopressin: Principles and Properties*, pp. 175-209, New York: Plenum Press, 1987). These components are then secreted into the circulation. SCLC tumors and cultured cells also express the VP gene, however intact provasopressin protein can become localized to the cell surface plasma membrane (Friedmann et al., *B. J. Cancer* 69: 260-263, 1994; North et al., *Ann. NY Acad. Sci.* 689: 107-121, 1993). Polyclonal antibodies raised against VP-NP bind specifically to the surface of cultured SCLC cells, as determined by immunofluorescent analysis (Friedmann et al., *Neuropeptides* 28: 183-189, 1995; North et al., *Prog. Brain Res.* 60: 217-225, 1983; North and Yu, *Regulatory Peptides* 45: 209-216, 1993). Thus, the target of these antibodies has been termed neurophysin-related cell surface antigen (NRSA) (North et al., *Peptides* 14: 303-307, 1993). Polyclonal anti-VP-NP antibodies recognize proteins of ~20 kDa and ~40 kDa in total protein extracts from SCLC cultured cells by Western analysis (North et al., *Peptides* 14: 303-307, 1993). The ~20 kDa protein corresponds in size to the provasopressin protein, and the ~40 kDa protein is believed to be a related form (Camier et al., *FEBS Lett.*, 108: 369-373, 1979; Lauber et al., *FEBS Lett.*, 97: 343-347, 1979; Lauber et al., *Proc. Natl. Acad. Sci. USA*, 78: 6086-6090, 1981; Moore and Rosenior, *Prog. Brain Res.* 60: 253-256, 1983; Nicolas et al., *Proc. Natl. Acad. Sci. USA*, 77: 2587-2591, 1980; Rosenior et al., *Endocrinology*, 109: 1067-1072, 1981). Polyclonal antibodies that have been raised against the vasopressin, VP-NP, or VAG regions of the pro-VP protein display specific staining of SCLC tumor sections, whereas they exhibit a very low incidence of immunoreactivity with the non-neuroendocrine lung tumors examined (Friedmann et al., *B. J. Cancer* 69: 260-263, 1994; Friedmann et al., *Cancer Letters* 75: 79-85, 1993).

Breast cancer is a leading cause of death among women throughout the world, and accounts for the death of approximately 50,000 women in the United States each year (American Cancer Society, *Cancer Facts and Figures*, Atlanta, Ga.: American Cancer Society, 1993). Although there have been many recent advances for effectively treating this disease (Silverstein, M. J. et al., *The Breast Journal* (2002) 8:70-76), successful intervention still heavily relies on early detection through mammography and surgical removal of cancerous tissue. As for small cell lung cancer (SCLC), products of the vasopressin (VP) gene appear to present a universal tumor marker system for breast cancer/ductal carcinoma in situ (DCIS) that could provide advanced warnings of early post-oncogenic tissue changes, precise methods for identifying and evaluating changes in tumor burden, and new non-surgical methods of treatment that are effective in providing long-term survival for patients (North et al. *Br. Can. Res. Treat.* (1995) 34: 229-235; and *North Exper. Physiol.* (2000) 85S: 27-40). Alternatively, no evidence has been found for expression by normal breast tissues or by various fibrocystic conditions, including atypical hyperdisplasia (North et al., *Endocrin. Pathology*, In Press, June, 2003). Expression of the VP gene in breast cancer gives rise to surface markers named GRSA (*North Exper. Physiol.* (2000) 85S: 27-40). These markers interact with polyclonal antibodies recognizing provasopressin and seem to have molecular weights of 40 and 20 kilodaltons. Since the antibodies were first found to interact with glycopeptide moiety of provasopressin, the antigen has been called GRSA (i.e., Glycopeptide-Related cell Surface Antigen).

SUMMARY OF THE INVENTION

Provided herein are antagonists (e.g., antibodies and antigen-binding portions thereof), for identifying and targeting provasopressin-expressing cancer cells. Also provided herein are methods of using compositions comprising such antagonists, for example, to image cancer cells in vivo and in biological samples. Said compositions may also be used for treating patients suffering from a provasopressin-expressing cancer. Provasopressin-expressing cancers include (but are not limited to) neuroendocrine cancer, pancreatic cancer, and prostate cancer.

The invention is based in part on the realization that the subject antagonists, e.g., antibodies or antigen-binding portions thereof, which bind provasopressin, are useful as therapeutic agents and/or diagnostic agents for provasopressin-expressing cancers, including certain pancreatic cancers, prostate cancers, and neuroendocrine cancers that express provasopressin.

Thus in one respect, the invention provides a method of treating a provasopressin (pro-VP)-expressing cancer, comprising administering a therapeutically effective amount of a provasopressin-binding antagonist (e.g., an antibody or antigen-binding portion thereof) to a patient in need thereof. In certain embodiments, the provasopressin-expressing cancer is not small cell lung cancer (SCLC) or breast cancer. In certain embodiments, the cancer is a neuroendocrine, prostate, or pancreatic cancer. In certain embodiments, the neuroendocrine cancer is a brain, gastroenteric, ovarian, endomedrial, testicular, adrenal, or skin cancer.

In a related aspect, the invention provides a method of treating a provasopressin-expressing (pro-VP-expressing) cancer, comprising administering, to a patient in need thereof, a therapeutically effective amount of a provasopressin-binding agent (such as an anti-provasopressin antibody or antigen-binding portion thereof, preferably MAG-1, MAG-2, MAG-3, MAG-4, MAG-5, or other antibodies similarly raised and having similar binding specificity/affinity), and a therapeutically effective amount of a pharmaceutical composition comprising a chemotherapeutic agent (such as cyclophosphamide or similar chemotherapeutic agents). In certain embodiments, the cancer is SCLC or breast cancer.

In certain embodiments, the provasopressin-binding antibody binds to the VAG region of the pro-VP protein. In certain embodiments, the provasopressin-binding antibody binds to the linker region of the pro-VP protein. In certain embodiments, the provasopressin-binding antibody binds to the VP-NP region of the pro-VP protein.

In certain embodiments, the provasopressin-binding antibody is a mouse antibody, a human antibody, a mouse-human chimeric antibody, a humanized antibody.

In certain embodiments, the antigen-binding portion thereof is scFv, Fab, F(ab')$_2$, Fd, Fv, or dAb.

In certain embodiments, the provasopressin-binding antibody is MAG-1, MAG-2, MAG-3, MAG-4, or MAG-5, or antibodies having similar binding specifity, including human antibody, humanized antibody, or chimeric antibody thereof. For example, the antibody may be a human antibody thereof, preferably having substantially the same or higher binding affinity; or a humanized antibody thereof, preferably having substantially the same or higher binding affinity); or a chimeric antibody thereof, preferably having substantially the same or higher binding affinity.

In certain embodiments, the antibody or antigen-binding portion thereof does not elicit a strong immune response from a patient. For instance, the antibody or antigen-binding portion thereof may have few or no epitopes recognized by human T cell receptors.

The methods herein may further comprise administering an effective amount of a pharmaceutical composition comprising a chemotherapeutic agent. This pharmaceutical composition comprising a chemotherapeutic agent may further comprise epinephrine. In some embodiments, the pharmaceutical compositions are administered concomitantly. In some embodiments, the pharmaceutical compositions are administered in a single formulation. Alternatively, the pharmaceutical compositions may be administered as separate formulations.

In certain embodiments, one may further administer an effective amount of a pharmaceutical composition comprising at least one of dexamethasone, IBMX, 8-bromoadenosine 3',5'-cyclic monophosphate (8br-cAMP), cyclophosphamide, cisplatin, etoposide VP-16 and forskolin.

The methods herein, in some embodiments, comprise performing surgical removal of at least one tumor from the patient. The methods may also comprise performing radiation therapy. The methods may further comprise administering a somatostatin analogue (e.g., those resistant to proteolytic enzymes and having longer half-lives, including Octreotide (SMS 201-995, Sandostatin), Somatuline (BIM 23014), Lanreotide, and RC 160 (Octastatin, Vapreotide), see de Herder et al., *Postgrad. Med. J.* 1996; 72: 403-408, incorporated by reference; also include pasireotide (SOM230), see Appetecchia and Baldelli, Endocrinology Unit, Regina Elena National Cancer Institute, Via Elio Chianesi, 53, Rome 00144, Italy), imatinib, sunitinib, temozolide, thalidomide, sorafenib, or panitumumab.

The antagonist (e.g., antibody or antigen-binding portion thereof) may further comprise a label. In certain embodiments, the label is selected from the group consisting of a fluorescent label, a radiolabel, a toxin, a metal compound, and biotin. In certain embodiments, the fluorescent label is selected from the group consisting of Texas Red, phycoerythrin (PE), cytochrome c, and fluorescent isothiocyanate (FITC). In other embodiments, the fluorescent label comprises a fluorescent protein or a protein that binds a fluorescent label. Examples of fluorescent proteins include dsRed, mRFP, YFP, GFP, CFP, BFP, and Venus. An example of a protein that binds a fluorescent label is FlAsH. In certain embodiments, the radiolabel is selected from the group consisting of $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi. In certain embodiments, the toxin is selected from the group consisting of ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Another aspect of the invention provides a method of killing provasopressin-expressing cancer cells, comprising contacting the provasopressin-expressing cancer cells with a provasopressin-binding antagonist (e.g., an antibody or an antigen-binding portion thereof). In certain embodiments, the provasopressin-expressing cancer cell is not a SCLC cell and not a breast cancer cell.

In a related aspect, the invention provides a method of killing a provasopressin-expressing cancer cell, comprising contacting the provasopressin-expressing cancer cell with a provasopressin-binding agent (such as an anti-proVP antibody or an antigen-binding portion thereof, preferably MAG-1 or other related MAG antibodies), and a chemotherapeutic agent (such as cyclophosphamide). In some embodiments, the provasopressin-expressing cancer cells are SCLC or breast cancer cells.

In a related aspect, the invention provides a method of inhibiting the growth and/or proliferation of provasopressin-expressing cancer cells, comprising contacting the provasopressin-expressing cancer cells with a provasopressin-binding antagonist (e.g., an antibody or an antigen-binding portion thereof). In some embodiments, the provasopressin-expressing cancer cells are not SCLC or breast cancer cells. In some embodiments, the provasopressin is on the surface of the provasopressin-expressing cancer cells.

In a related aspect, the invention provides a method of inhibiting the growth of a provasopressin-expressing cancer cell, comprising contacting the provasopressin-expressing cancer cell with a provasopressin-binding agent (such as an anti-pro-VP antibody or an antigen-binding portion thereof, preferably MAG-1 or other related MAG antibodies), and a chemotherapeutic agent (such as cyclophosphamide). In some embodiments, the provasopressin-expressing cancer cells are SCLC or breast cancer cells.

Another aspect of the invention also provides a method of phenotyping biological samples from patients having a provasopressin-expressing cancer, other than breast cancer or small cell lung cancer, the method comprising: (a) obtaining a biological sample from a patient, optionally rendering the biological sample amenable to immunoassay; (b) contacting the sample with a provasopressin-binding antagonist (e.g., an antibody or antigen-binding portion thereof), under conditions that allow for binding of the antagonist to provasopressin; and (d) determining if the cells of the sample inappropriately express provasopressin compared to a control tissue; wherein if the test tissue inappropriately expresses provasopressin, the biological sample is identified as likely having cancerous cells.

Another related aspect of the invention provides a method of identifying a patient suitable for treatment with the subject binding agent specific for provasopressin, by diagnosing the presence in a patient a tumor/cancer expressing provasopressin, the method comprising: a) obtaining a biological sample (such as a biopsy) from the patient; b) if necessary, rendering the biological sample amenable to immunoassay; c) contacting the sample with an antibody or an antigen-binding portion thereof specific for provasopressin, under conditions that allow for binding of the antibody or antigen-binding portion to provasopressin; and d) determining if the cells of the sample expresses a significantly higher level of provasopressin compared to a control tissue; wherein the patient is selected for treatment with the subject binding agent specific for provasopressin if the cells of the sample express a significantly higher level of provasopressin compared to the control tissue. Preferably, the method further comprises treating the identified/selected patient by administering to the patient one or more of the subject binding agent specific for provasopressin, with or without a second therapy.

In some embodiments, if the test tissue shows inappropriate provasopressin expression, a therapeutically effective amount of a provasopressin-binding antagonist (e.g., antibody or antigen-binding portion thereof) is administered to the patient.

In some embodiments, before step (a), the patient has been diagnosed as having a provasopressin-expressing cancer, such as prostate cancer, pancreatic cancer, or neuroendocrine cancer.

Another aspect of the invention also provides a kit useful for screening a biological sample for a provasopressin-expressing cancer other than breast cancer or small cell lung cancer, comprising a provasopressin-binding antagonist (e.g., antibody or antigen-binding portion thereof). The kit may be labeled for use in detecting a provasopressin-expressing cancer such as prostate cancer, pancreatic cancer, or neuroendocrine cancer. The kit may also include instructions stating that the kit is for use in diagnosing a provasopressin-expressing cancer such as prostate cancer, pancreatic cancer, or neuroendocrine cancer.

Another aspect of the invention provides a method of detecting a tumor in a patient having a provasopressin-expressing cancer other than breast cancer or small cell lung cancer, the method comprising: (a) administering a pharmaceutical composition comprising a provasopressin-binding antagonist (e.g., antibody or antigen-binding portion thereof) to the patient, (b) detecting the label, and (c) determining if the patient has cells that inappropriately express provasopressin compared to a control; wherein if the patient has cells that inappropriately express provasopressin, the patient is identified as likely having a tumor.

Another related aspect of the invention provides a method of identifying a patient suitable for treatment with the subject binding agent specific for provasopressin, by detecting a tumor in a patient having a provasopressin-expressing cancer other than breast cancer or small cell lung cancer, the method comprising: (a) administering a pharmaceutical composition comprising a provasopressin-binding antagonist (e.g., antibody or antigen-binding portion thereof) to the patient, (b) detecting the label, and (c) determining if the patient has cells that inappropriately express provasopressin compared to a control; wherein if the patient has cells that inappropriately express provasopressin, the patient is identified as likely having a tumor and is identified as suitable for treatment with the subject binding agent specific for provasopressin.

In certain embodiments, the method further comprises, if the patient has cells that inappropriately express provasopressin, administering a therapeutically effective amount of a provasopressin-binding antagonist (e.g., antibody or antigen-binding portion thereof) to the patient.

In certain embodiments, before step (a), the patient has been diagnosed as having a provasopressin-expressing cancer.

The method may further comprise determining the location and/or volume of a plurality cells inappropriately expressing provasopressin (for example, determining the volume of a tumor). This method may be used to determine the location of a tumor prior to surgical resection of the tumor. It may also be used to determine whether surgery is appropriate.

In some embodiments, the cancer is not SCLC or breast cancer. In some embodiments, the cancer is not ductal carcinoma in situ (DCIS)—a type of breast cancer.

Provasopressin-binding antibodies may have, for example, at least 70%, 75%, 80%, 85%, 90%, 95%, 97%, 98%, 99%, or 100% amino acid sequence identity to MAG-1, MAG-2, MAG-3, MAG-4, or MAG-5. In certain embodiments, the antibodies may have variable regions that have at least 70%, 75%, 80%, 85%, 90%, 95%, 97%, 98%, 99%, or 100% amino acid sequence identity to the variable regions of MAG-1, MAG-2, MAG-3, MAG-4, or MAG-5.

The antibody or antigen-binding portion thereof may comprise the complementary determining regions (CDR) of the antibody or antigen-binding portion of the disclosed antibodies, and human framework regions.

Another aspect of the invention provides a method of treating a neuroendocrine cancer, comprising administering a therapeutically effective amount of a provasopressin-binding antibody or antigen-binding portion thereof to a patient in need thereof, wherein the cancer is not small cell lung cancer.

Another aspect of the invention provides a method of killing neuroendocrine cancer cells, comprising contacting the neuroendocrine cancer cells with a provasopressin-binding antibody or an antigen-binding portion thereof, wherein the neuroendocrine cancer cells are not small cell lung cancer cells.

Another aspect of the invention provides a method of inhibiting the growth of neuroendocrine cancer cells, comprising contacting the neuroendocrine cancer cells with a provasopressin-binding antibody or an antigen-binding portion thereof, wherein the neuroendocrine cancer cells are not small cell lung cancer cells. In certain embodiments, the cancer cells express provasopressin.

The potential uses for methods of administering anti-provasopressin antagonists (e.g., antibodies and antigen-binding portions thereof) are not limited to therapeutic use, but also includes basic research use. For example, the antagonists may be used in tissue culture or in a model organism to study the mechanism by which anti-provasopressin antibodies inhibit cancer.

It is contemplated that any embodiment of the invention can be combined with any other embodiment(s), including embodiment(s) described under different aspects of the invention.

BRIEF DESCRIPTION OF THE DRAWINGS

FIG. 2A illustrates staining with MAG-1 mAb or MAG-1 Fab. FIG. 2B illustrates staining with MAG-1 mAb or a rabbit polyclonal antibody against VP-NP. Approximate molecular mass is indicated on the left of each figure. Total cellular or tissue protein extracts (40 μg) were separated by SDS-PAGE, blotted onto polyvinylidene difluoride (PDVF) membrane, and reacted with (FIG. 2A) MAG-1 mAb or MAG-1 Fab, and with (FIG. 2B) MAG-1 mAb or a rabbit polyclonal antibody against VP-NP.

FIGS. 3A-3D show flow cytometry analysis of MAG-1 binding to the surface of cultured SCLC cells. FIG. 3A illustrates MAG-1 Fab staining of NCI-H82 cells at two different concentrations compared to a control IgG1 antibody. FIG. 3B illustrates MAG-1 mAb staining of NCI-H345 cells compared to a control IgG1 antibody. FIG. 3C illustrates MAG-1 mAb staining of NCI-H82 cells at two different concentrations compared to a control IgG1 antibody. FIG. 3D illustrates MAG-1 mAb staining of Lu165 cells compared to a control IgG1 antibody. Antibody staining procedures prior to flow cytometry were performed using conditions that minimize plasma membrane internalization. MAG-1 mAb and MAG-1 Fab were employed at a concentration of 100 μg/ml except where noted.

FIGS. 4A-4C show confocal analysis of MAG-1 binding to the surface of cultured SCLC cells. SCLC cells were reacted with MAG-1 or an isotype control mAb, followed by FITC-labeled secondary antibodies. FIG. 4A illustrates combined differential interference contrast (DIC) transmitted, red fluorescent, and green fluorescent light channel images of NCI-H82 cells viewed with a 40× objective (NA 1.4) and a 5.8× magnification zoom setting. The cells were incubated with propidium iodide to stain the nuclei (gray) for contrast. FIG. 4B NCI-H345 illustrates imaged by confocal microscopy and the top panels display the control IgG1 observed with a 20× objective (0.5 NA) and the lower panels display the MAG-1 stained cells observed with a 40× objective (1.3 NA). FIG. 4C illustrates Lu-165 cells imaged by confocal microscopy with a 40× objective. For FIGS. 4B and 4C, the left panels depict the transmitted light channel images, the middle panes depict the green fluorescent light channel images, and the right panels depict the two combined images.

FIG. 5A depicts MAG-1 immunoreactivity with human SCLC tumor cells (brown staining). FIG. 5B depicts control normal epithelial cells of the alveoli of the lung. FIG. 5C depicts control normal epithelial cells of the bronchioles of the lung.

FIGS. 6A and 6B illustrate the amino acid sequence and nucleic acid sequence of a single chain variable fragment immunoreactive with the C-terminal 18-amino acid residues of VAG. FIG. 6A depicts the amino acid sequence (SEQ ID NO: 2). FIG. 6B depicts the nucleic acid sequence (SEQ ID NO: 3).

FIGS. 13A-13E show confocal images of cell surface localization of the GRSA antigen in prostate cancer cell line PC3.

FIGS. 16A and 16B show internalization of the mMAG-1 antibody (FIG. 16A) and the 520C-9 positive control antibody (FIG. 16B) in SKBr3 cells.

FIG. 17 shows synergistic inhibition of SCLC H82 tumor growth after chemotherapy with cyclophosphamide and treatment with mMAG-1.

DETAILED DESCRIPTION

1. Overview

Figure 1:
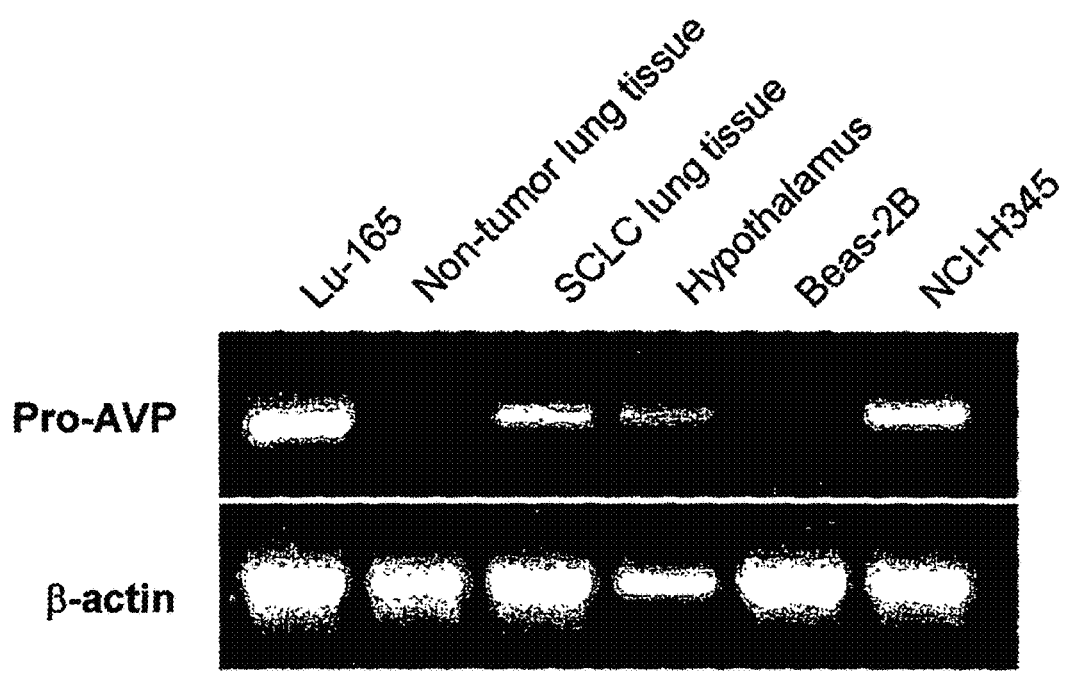
FIG. 1 illustrates detection of NRSA in cultured SCLC cells and human SCLC tissue by RT-PCR analysis. RT-PCR was performed on total RNA extracts from the indicated cell lines or human tissue. Products were separated on a 1.5% agarose gel and visualized with ethidium bromide. The PCR primers were designed to amplify the entire coding region for the pro-VP protein, which spans 2 introns. The predicted size for the amplification is 570 bp. Lu-165 and NCI-H345; SCLC cell lines, Beas-2B; transformed normal human epithelial cell line, lung and hypothalamus; human tissue extracts were tested.

The present disclosure describes, inter alia, the detection of NRSA in provasopressin-expressing cancers using pro-vasopressin-binding antibodies, such as MAG-1, MAG-2, MAG-3, MAG-4, and MAG-5, antigen-binding portions thereof, and other related forms of antibodies or mimics thereof. These antibodies may bind the C-terminal portion of the VAG region of provasopressin, and may have similar specificity and/or affinity as that of MAG-1.

MAG-1 was described in PCT Publication No. WO04/006860, which is herein incorporated by reference in its entirety. MAG-2 through MAG-5 have been described in more detail in U.S. Provisional Application 61/127,089 and PCT publication WO 2009/137113A2, which are both incorporated herein by reference in their entirety. Exemplary methods for producing such antibodies have been described in more details below.

MAG-1 recognizes the ~20 kDa and ~40 kDa NRSA proteins in cultured SCLC cell lysate by Western analysis, while immunofluorescent cytometric and microscopic analyses indicates that it binds to the surface of these cells. The ~20 kDa and ~40 kDa NRSA proteins were detected in the lysate of human SCLC tumor biopsy samples by Western analysis using MAG-1, but they were not detected in the lysate of non-tumor human lung tissue.

Immunohistochemical analysis revealed that MAG-1 reacts with human SCLC tumor, but not with normal lung tissue. Since NRSA is not typically found on the surface of normal cells, it is an excellent target in an antibody-based approach for tumor localization in the diagnosis and therapy of cancers expressing NRSA, such as neuroendocrine, prostate, and pancreatic cancers.

Thus the invention described herein provides reagents and methods of using such reagents for treating or diagnosing patients having pro-VP expressing cancer or tumor.

The description in the sections below provide more details concerning the different aspects of the invention, which aspects may be combined with one another without restriction unless explicitly disclaimed.

2. Definitions

"Administering," "administration," or other grammatical variations is defined herein as providing a composition to a patient in a manner that results in the composition coming into contact with the patient's body, in a manner that permits or leads to a desired therapeutic effect. Such an administration can be by any route, including, without limitation, subcutaneous, intradermal, intravenous, intra-arterial, intra-peritoneal, intramuscular, and/or topical.

The term "amino acid residue" is known in the art. In general, the abbreviations used herein for designating the amino acids and the protective groups are based on recommendations of the IUPAC-IUB Commission on Biochemical Nomenclature (see *Biochemistry* (1972) 11:1726-1732). In certain embodiments, the amino acids used are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan. In other embodiments, an amino acid may be modified by post-translational modifications, such as glycosylation, phosphorylation, deamidation, isomerization, pyroglutamic acid modification, and oxidation (e.g., methionine oxidation).

As used herein, the term "antibody" refers to an immunoglobulin molecule. The term "antibody" encompasses monoclonal and polyclonal antibodies. The antibody may be an IgG, an IgM, an IgE, an IgA or an IgD molecule. In certain embodiments, the antibody is an IgG and is an IgG1, IgG2, IgG3 or IgG4 subtype. The class and subclass of antibodies may be determined by any method known in the art, for example, by using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant domains of the heavy and/or light chains of the antibodies, comparing their amino acid sequences to the known amino acid sequences of various class and subclasses of immunoglobulins, and determining the class and subclass of the antibodies.

As used herein, the term "antibodies" encompasses immunoglobulins produced in vivo, as well as those produced in vitro by, for example, a hybridoma, and antigen binding fragments (e.g., Fab' preparations) of such immunoglobulins, as well as to recombinantly expressed antigen binding proteins, including immunoglobulins, chimeric immunoglobulins, "humanized" immunoglobulins such as COMPOSITE HUMAN ANTIBODIES™ immunoglobulins, antigen binding portions of such immunoglobulins, single chain antibodies, and other recombinant proteins containing antigen binding domains derived from immunoglobulins. As used herein, in certain embodiments, "antibodies" also include antigen binding synthetic peptides comprising sequences derived from the sequences of immunoglobulin antigen binding domains. In other embodiments, "antibodies" exclude such antigen binding synthetic peptides. In some embodiments, the anti-vasopressin antibody or antigen-binding portion thereof contains non-natural amino acid residues and/or is conjugated to additional molecules such as PEG.

The term "human antibody," as used herein, is intended to include antibodies having variable and constant regions obtained or derived from human germline immunoglobulin sequences. The human antibodies of the invention may include amino acid residues not encoded by human germline immunoglobulin sequences or sequences of actual human DNA (e.g., human antibodies of the invention may include amino acid mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "recombinant human antibody," as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor, L. D., et al. (1992) *Nucl. Acids Res.* 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

An "isolated antibody," as used herein, is intended to refer to an antibody that is substantially free of other antibodies having different antigenic specificities (e.g., an isolated antibody that specifically binds abnormal vasopressin V2 receptor is substantially free of antibodies that specifically bind antigens other than the abnormal vasopressin V2 receptor, including the wild-type vasopressin V2 receptor). An isolated antibody that specifically binds abnormal vasopressin V2 receptor may, however, have cross-reactivity to other antigens, such as abnormal vasopressin V2 receptor molecules from other species. Moreover, an isolated antibody may be substantially free of other cellular material and/or chemicals.

As used herein, the "antigen-binding portion thereof" of an anti-provasopressin antibody refers to a portion of an anti-provasopressin antibody that binds to provasopressin with substantial affinity. Substantial affinity includes affinity that is at least $\frac{1}{100}$, $\frac{1}{50}$, $\frac{1}{20}$, $\frac{1}{10}$, $\frac{1}{5}$, or $\frac{1}{2}$ the affinity of the (native) antibody for provasopressin. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide.

As used herein, "biological sample" refers to a sample taken from the body of a patient. Such samples include tissue biopsy sample, blood samples, urine samples, and the like.

"Boris," as used herein, refers to the polyclonal antibody preparation reactive with vasopressin-human glycopeptide (VAG), the preparation of which is described in North et al. *Breast Cancer Res Treat.* 34(3): 229-35, 1995).

As used herein, the term "cancer" refers to a condition in which a cell in a patient's body undergoes abnormal, uncontrolled proliferation. "Cancer" also refers to cancerous or malignant tumor tissues. In certain embodiments, the cancer is malignant. Non-limiting examples of cancers include SCLC, breast cancer, ovarian cancer.

As used herein, the term "tumor" is used to mean a condition in which a cell in a patient's body undergoes abnormal, uncontrolled proliferation. In certain embodiments, the tumor is malignant. In certain embodiments, the tumor is benign. Non-limiting example of tumor include hyperplasia.

"Homology" is a measure of the identity of nucleotide sequences or amino acid sequences. In order to characterize the homology, subject sequences are aligned so that the highest percentage homology (match) is obtained, after introducing gaps, if necessary, to achieve maximum percent homology. N- or C-terminal extensions shall not be construed as affecting homology. "Identity" per se has an art-recognized meaning and can be calculated using published techniques. Computer program methods to determine identity between two sequences, for example, include DNAStar® software (DNAStar Inc. Madison, Wis.); the GCG® program package (Devereux, J., et al. *Nucleic Acids Research* (1984) 12(1): 387); BLASTP, BLASTN, FASTA (Atschul, S. F. et al., *J. Molec. Biol.* (1990) 215: 403). Homology (identity) as defined herein is determined conventionally using the well-known computer program, BEST-FIT® (Wisconsin Sequence Analysis Package, Version 8 for Unix, Genetics Computer Group, University Research Park, 575 Science Drive, Madison, Wis., 53711). When using BESTFIT® or any other sequence alignment program (such as the Clustal algorithm from MegAlign software (DNAS-TAR®) to determine whether a particular sequence is, for example, about 90% homologous to a reference sequence, the parameters are set such that the percentage of identity is calculated over the full length of the reference nucleotide sequence or amino acid sequence and that gaps in homology of up to about 90% of the total number of nucleotides in the reference sequence are allowed.

A "humanized" antibody or antigen-binding portion thereof, as used herein, is an antibody originally generated in a non-human animal, where the non-human animal content (especially the portion not directly responsible for antigen-binding, e.g., the non-CDR region) has been reduced or replaced by corresponding human sequence, by altering the original amino acid sequence, or a fragment of the antibody. The non-human animal content may be less than 50%, 40%, 30%, 20%, 10%, or 5%. In certain humanized antibodies, the six CDRs of the heavy and light chains and a limited number of structural amino acids of the murine monoclonal antibody are grafted by recombinant technology to the CDR-depleted human IgG scaffold. A humanized antibody may also be a fully human antibody, which may be made in humanized mice resulting in antibodies that do not contain any mouse sequences. In certain embodiments, chimeric, humanized or primatized (CDR-grafted) antibodies, comprising portions derived from different species or fully human antibodies, are also encompassed by the present disclosure. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S.

Pat. No. 4,816,567; Cabilly et al., European Patent No. 0,125,023; Boss et al., U.S. Pat. No. 4,816,397; Boss et al., European Patent No. 0,120,694; Neuberger, M. S. et al., WO 86/01533; Neuberger, M. S. et al., European Patent No. 0,194,276 B1; Winter, U.S. Pat. No. 5,225,539; and Winter, European Patent No. 0,239,400 B1. See also, Newman, R. et al., BioTechnology, 10: 1455-1460 (1992), regarding primatized antibody. See, e.g., Ladner et al., U.S. Pat. No. 4,946,778; and Bird, R. E. et al., Science, 242: 423-426 (1988)), regarding single chain antibodies.

As used herein, the term "inappropriately express" refers to substantial expression of a gene (or protein) that occurs in a cell type that does not ordinarily substantially express that gene (or protein). Provasopressin is normally expressed only in the hypothalamus, so substantial expression of provasopressin outside the hypothalamus is considered inappropriate expression of provasopressin. In certain embodiments, when the expression difference is quantitative, the expression levels are preferably statistically significantly different (e.g., $p<0.05$, or $p<0.01$).

As used herein, the term "label" or "labeled" refers to incorporation of another molecule in the antibody, antigen-binding portion thereof, or peptide. In one embodiment, the label is a detectable marker, e.g., incorporation of a radiolabeled amino acid. Various methods of labeling polypeptides and glycoproteins are known in the art and may be used. Examples of labels for polypeptides include, but are not limited to, the following: radioisotopes or radionuclides, fluorescent labels, enzymatic labels, chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, and toxins.

"MAG-1" as used herein refers to the monoclonal antibody that is produced by the hybridoma having ATCC Number PTA-5322.

A "patient" or "subject" to be treated by the subject methods may mean either a human or non-human animal, such as primates, mammals, vertebrates, rodents, etc.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient, within a reasonable risk-benefit ratio. In certain embodiments, a pharmaceutically acceptable carrier is non-pyrogenic.

As used herein, "provasopressin-binding antibody" refers to an antibody that binds provasopressin with high affinity. Exemplary provasopressin-binding antibodies include MAG-1 (described in US Application Publication No. 2008-0050376 and produced by the hybridoma having ATCC Number PTA-5322), MAG-2, MAG-3, MAG-4, and MAG-5. In certain embodiments, the provasopressin-binding antibodies include Boris and humanized antibodies derived from Boris. In certain embodiments, the provasopressin-binding antibodies include antibodies having CDR-H3 and CDR-L3 regions identical to that of any one of MAG-1, MAG-2, MAG-3, MAG-4, or MAG-5. In certain embodiments, the provasopressin-binding antibodies include antibodies having CDR-H1, CDR-H2, CDR-H3, CDR-L1, CDR-L2, and CDR-L3 regions identical to that of any one of MAG-1, MAG-2, MAG-3, MAG-4, or MAG-5. In certain embodiments, the provasopressin-binding antibodies include antibodies having LCVR (light chain variable region) and HLVR (heavy chain variable region) identical to that of any one of MAG-1, MAG-2, MAG-3, MAG-4, or MAG-5. In certain embodiments, the provasopressin-binding antibodies include antibodies having a single Ala substitution in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having 2, 3, 4, or 5 Ala substitutions in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having a single conserved amino acid substitution in any one of the CDR3 residues in the light chain and/or heavy chain sequence of any one of MAG-1, MAG-2, MAG-3, MAG-4, or MAG-5. In certain embodiments, the provasopressin-binding antibodies include antibodies having 2, 3, 4, or 5 conserved amino acid substitutions in any one of the CDR3 residues in the light chain and/or heavy chain sequence of any one of MAG-1, MAG-2, MAG-3, MAG-4, or MAG-5. Preferably, no more than one to five conservative amino acid substitutions are made within the VL and/or VH CDR3 domains. More preferably, no more than one to three conservative amino acid substitutions are made within the VL and/or VH CDR3 domains. Additionally, conservative amino acid substitutions (excluding Ala substitution) are not made at amino acid positions critical for antigen binding (e.g., those positions the substitution of which results in at least about 10-fold loss/increase in $K_d$ and/or $k_{off}$ values).

A "conservative amino acid substitution," as used herein, is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). See Table A below for exemplary conservative substitutions.

Provasopressin-binding antibodies may also include single chain (scFv) antibodies. The antibodies herein may be IgG antibodies, including IgG1, IgG2, IgG3, or IgG4 antibodies. In some embodiments, the antibody binds to provasopressin selectively.

The term "provasopressin-expressing cancer" as used herein refers to a cancer that displays substantial expression of provasopressin. The cancer may, for example, express at least 2, 5, 10, 20, 50, 100, 200, 500, or 1000-fold more provasopressin than a corresponding wild-type tissue. The cancer may be benign or malignant, may be (locally) invasive and/or metastatic. As used herein, "provasopressin-expressing cancer" preferably expresses provasopressin on the surface of cancer/tumor cells. Expression of provasopressin in a cancer or tumor sample (e.g., in at least some, but not necessarily all cells within the cancer/tumor tissue) may be determined by any of art recognized methods, including immunohistochemistry, Westernblot, etc. In certain embodiments, the cancer is not small cell lung cancer (SCLC) or breast cancer.

The term "selective" or "selectively," as used herein in the context of selective binding, refers to a macromolecule (such as an antibody or antigen-binding portion thereof) that binds to its desired target (provasopressin of a fragment thereof) with a $K_d$ that is less than 2-fold, 5-fold, and preferably 10-, 20-, 50-, 100-, 200, 500-, or 1000-fold the $K_d$ of that antibody or antigen-binding portion thereof for any other wild-type human protein.

A "therapeutically effective amount" refers to an effective amount of composition for causing a respective desired therapeutic effect, such as the tumor-/cancer-specific killing of tumor or cancer cells in a patient, eliminating one or more tumor/cancer cells, preventing said cells from proliferating, or inhibiting the rate of proliferation of said cells. Preferably, the therapeutically effective amount possesses a reasonable benefit/risk ratio applicable to the medical treatment.

By "treating" a patient suffering from tumor/cancer, it is meant that at least one of the patient's symptoms is partially or totally alleviated, remain static, or its progression retarded, following treatment according to the methods herein. A patient that has been treated can exhibit a partial or total alleviation of symptoms and/or tumor load, either temporarily or permanently. In certain embodiments, the term "treatment" may encompass prophylaxis use, therapy and cure. In certain embodiments, the term "treatment" may exclude prophylaxis use, therapy and cure.

3. Antibodies and Antigen-binding Portions Thereof
3.1 Exemplary Provasopressin-binding Antibodies The methods herein may use various provasopressin-binding agents, such as anti-proVP binding antibodies or antigen-binding portions thereof.

As used herein, "provasopressin-binding antibody" include monoclonal or polyclonal antibodies. Such antibodies may be mouse antibodies, human antibodies, chimeric antibodies (such as human-mouse chimeric antibodies), or humanized antibodies. The antigen-binding portion thereof may include single chain scFv, Fab, F(ab')$_2$, Fd, Fv, dAb, bispecific antibodies, or other antibody fragments that retains all or substantially all binding affinity (e.g., no worse than 5, 10, 20, 50, 100, 200, 500 fold reduction, as measured by $K_d$ and/or $k_{off}$) of a full length antibody, such as an IgG1, IgG2, IgG3, or IgG4 antibody.

The antibody or its antigen-binding portion thereof may bind, preferably specifically, to any epitope of the GRSA or NRSA antigen or pro-VP, including the mature VP region, mature VP-NP region, mature VAG region, or linker regions therebetween (such as the link between vasopressin and neurophysin moieties). The antibody may also be specific for epitopes comprising post-translational modifications, including glycosylation.

In certain embodiments, the antibody may be in its native form. In certain embodiments, the antibody may be in forms containing a covalently or non-covalently conjugated moiety, such as an attached toxin, enzyme, fluorescent label, or radionuclide.

In some embodiments, the antibody or antigen-binding portion thereof comprises a purification tag. A purification tag may be used to facilitate purification of the antibody or antigen-binding portion thereof during the manufacturing process. Exemplary purification tag peptides include His, GST, TAP, FLAG, myc, HA, MBP, VSV-G, thioredoxin, V5, avidin, streptavidin, BCCP, Calmodulin, Nus, and S tags.

One exemplary antibody MAG-1 interacts with the GRSA antigen, a form of provasopressin present as a surface product on pro-VP expressing cancers.

The subject antibody or antigen-binding portion thereof may be immunoreactive with the isolated polypeptide of SEQ ID NO: 1, SEQ ID NO: 5, and/or SEQ ID NO: 6.

Provasopressin-binding antibodies include the monoclonal antibody produced by the hybridoma having ATCC Number PTA-5322, wherein the monoclonal antibody is MAG-1. Provasopressin-binding antibodies also include the similarly produced monoclonal antibodies MAG-2, MAG-3, MAG-4, and MAG-5 (see below).

In certain embodiments, the provasopressin-binding antibody is selective for provasopressin. In other embodiments, the provasopressin-binding antibody is selective for a particular epitope of provasopressin. For example, it may immunoreact with SEQ ID NO: 1 but show no substantial immunoreactivity with SEQ ID NO: 6. Other provasopressin-binding antibodies immunoreact with SEQ ID NO: 6, but show no substantial immunoreactivity SEQ ID NO: 1.

In certain embodiments, the subject antibody may also include variants of the MAG-1, MAG-2, MAG-3, MAG-4, and/or MAG-5 antibodies. Variants of these antibodies, or antigen-binding portions thereof, and peptides may have an amino acid sequence that is different by one or more amino acid substitutions from the amino acid sequence of MAG-1, MAG-2, MAG-3, MAG-4, or MAG-5. Embodiments which comprise amino acid deletions and/or additions are also contemplated. The variant may have conservative changes (amino acid similarity), wherein a substituted amino acid has similar structural or chemical properties, for example, the replacement of leucine with isoleucine. Guidance in determining which and how many amino acid residues may be substituted, inserted, or deleted without abolishing biological or proposed pharmacological activity may be reasonably inferred in view of this disclosure and may further be found using computer programs well known in the art, for example, DNASTAR® software.

Amino acid substitutions may be made, for instance, on the basis of similarity in polarity, charge, solubility, hydrophobicity, hydrophilicity, and/or the amphipathic nature of the residues as long as a biological and/or pharmacological activity of the native molecule is retained.

Negatively charged amino acids include aspartic acid and glutamic acid; positively charged amino acids include lysine and arginine; amino acids with uncharged polar head groups having similar hydrophilicity values include leucine, isoleucine, and valine; amino acids with aliphatic head groups include glycine, alanine; asparagine, glutamine, serine; and amino acids with aromatic side chains include tryptophan, phenylalanine, and tyrosine.

Example substitutions are set forth in Table A as follows:

TABLE A

| Original Residue | Example conservative substitutions |
|---|---|
| Ala (A) | Gly; Ser; Val; Leu; Ile; Pro |
| Arg (R) | Lys; His; Gln; Asn |
| Asn (N) | Gln; His; Lys; Arg |
| Asp (D) | Glu |
| Cys (C) | Ser |
| Gln (Q) | Asn |
| Glu (E) | Asp |
| Gly (G) | Ala; Pro |
| His (H) | Asn; Gln; Arg; Lys |
| Ile (I) | Leu; Val; Met; Ala; Phe |
| Leu (L) | Ile; Val; Met; Ala; Phe |
| Lys (K) | Arg; Gln; His; Asn |
| Met (M) | Leu; Tyr; Ile; Phe |
| Phe (F) | Met; Leu; Tyr; Val; Ile; Ala |
| Pro (P) | Ala; Gly |

TABLE A-continued

| Original Residue | Example conservative substitutions |
| --- | --- |
| Ser (S) | Thr |
| Thr (T) | Ser |
| Trp (W) | Tyr; Phe |
| Tyr (Y) | Trp; Phe; Thr; Ser |
| Val (V) | Ile; Leu; Met; Phe; Ala |

3.2 Humanized Antibodies and Human Antibodies

One problem that antibody engineering attempts to address is the immune activity of a human patient that occurs in response to a native murine (or other non-human animal) antibody, typically a mAb, that is being administered to the patient for therapeutic purposes. This activity against murine antibodies is characterized by a human anti-mouse antibody (HAMA) response that can have deleterious effects on treatment efficacy and patient health. The HAMA response may be triggered when an antibody has epitopes recognized by human T cells. Thus, the antibodies described herein preferably are not recognized well by human T cells.

It has been found that almost all such human anti-non-human antibody ("HAMA type") activity is directed at the constant domains and at the FR regions of the variable domains of native non-human antibodies. Antibodies from other non-human animals have similar deleterious effects to a patient. The antibodies described herein may be humanized by any means known in the art.

By manipulating the nucleic acid molecules encoding antibody H and L chains, it is possible to incorporate non-human variable regions into antibodies otherwise made up of human constant regions. The resulting antibodies are referred to as "chimeric antibodies," and are typically less prone to eliciting HAMA type responses than are the non-human antibodies from which the variable regions are derived.

An alternative to eliminating the potential of a non-human antibody to elicit a HAMA type response is to "humanize" it, i.e., to replace its non-human framework regions with human ones. One way of achieving such humanization involves the insertion of polynucleotide fragments encoding the non-human CDRs of the antibody to be humanized into a nucleic acid molecule encoding an otherwise human antibody (with human constant regions if desired) so as to replace the human CDRs and to use the resulting nucleic acid molecule to express the encoded "humanized" antibody. If this process results in a loss of antibody-epitope affinity, selected humanized residues may be mutated back to their identity in the non-human antibody.

Detailed discussions of antibody engineering may be found in numerous recent publications including: Borrebaek, *Antibody Engineering, A Practical Guide,* 1992, W.H. Freeman and Co. NY; and Borrebaek, *Antibody Engineering,* 2nd ed. 1995, Oxford University Press, NY, Oxford (incorporated by reference).

A humanized antibody can be an antibody derived from a non-human species, in which certain amino acids in the framework and constant domains of the heavy and light chains have been mutated so as to reduce or abolish an immune response in humans. Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293 (incorporated by reference). A humanized antibody may comprise portions of immunoglobulins of different origin. For example, at least one portion can be of human origin. For example, the humanized antibody can comprise portions derived from an immunoglobulin of non-human origin with the requisite specificity, such as a mouse, and from immunoglobulin sequences of human origin (e.g., a chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Alternatively, a humanized antibody may be created in a transgenic or humanized animal expressing the human antibody genes (see Lonberg, N. "Transgenic Approaches to Human Monoclonal Antibodies," *Handbook of Experimental Pharmacology* (1994)113: 49-101) (incorporated by reference).

Another example of a humanized immunoglobulin is an immunoglobulin containing one or more immunoglobulin chains comprising a CDR of non-human origin (e.g., one or more CDRs derived from an antibody of nonhuman origin) and a framework region derived from a light and/or heavy chain of human origin (e.g., CDR-grafted antibodies with or without framework changes). Chimeric or CDR-grafted single chain antibodies are also encompassed by the term humanized immunoglobulin.

One means of humanization is called COMPOSITE HUMAN ANTIBODY™ technology, which is described in detail in WO 2006/082406 (incorporated by reference). Briefly, the CDR regions are left intact or essentially intact. The non-human framework is replaced with a composite humanized framework. The composite humanized framework may be a chimera of several fragments from different endogenous human framework alleles. In this manner, a composite framework may be produced that resembles the antibody's non-human framework more closely than any given endogenous human framework.

In certain embodiments, the antibody of the invention may be fully human antibodies, such as isolated human antibodies. An entirely human antibody should, in theory, not elicit the HAMA reaction, even if used for prolonged periods. Fully human monoclonal autoantibodies may be prepared using human hybridoma techniques (see Boyle et al., *Cell. Immunol.* 152: 556-568, 1993; Boyle et al., *Cell. Immunol.* 152: 569-581, 1993; European Patent Application Publication No. 614 984 A2 by Boyle, et al.). Preferably, the human antibodies have a high affinity for its antigen, which affinity can be measured or calculate by conventional methods, such as Kd or koff values that can be measured by surface plasmon resonance.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 and Jonsson, U., et al. (1993) *Ann. Biol. Clin.* 51:19-26; Jonsson, U., et al. (1991) *Biotechniques* 11:620-627; Johnsson, B., et al. (1995) *J. Mol. Recognit.* 8:125-131; and Johnnson, B., et al. (1991) *Anal. Biochem.* 198:268-277.

Alternatively, the subject human antibodies may be produced by recombinant DNA technology using procedures well known in the art. Recombinant human antibodies preferably have high affinity (e.g., $K_d$ is about $10^{-7}$ M, $10^{-8}$ M, $10^{-9}$ M, $10^{-10}$ M or less) and a slow $k_{off}$ rate (e.g., $k_{off}$ is about $10^{-2}$ s$^{-1}$, $10^{-3}$ s$^{-1}$, $10^{-4}$ s$^{-1}$, $10^{-4}$ s$^{-1}$).

Methods of producing and selecting fully human antibody are well known in the art. See, for example, U.S. Pat. Nos.

4,800,155; 5,087,557; 5,196,337; 5,767,246; 6,090,383; 6,139,869; 6,787,153; 7,005,503 (all incorporated herein by reference).

3.3 Non-antibody Binding Agents

Although the subject pro-VP antagonists include antibodies, antigen-binding portions thereof, and variants thereof with amino acid sequence substitutions, the antagonists are not so limited. Other antagonists, including protein or nucleic acid based antagonists, may also be used in the subject methods.

In certain embodiments, the pro-VP antagonist is an aptamer. Since the identification of the first RNA aptamer as an antagonist against bacterial phage T4 DNA polymerase in 1990, the SELEX (systematic evolution of ligands by exponential enrichment) process and its variations have been used successfully to identify aptamers for more than 100 diverse target molecules, including organic dyes, amino acids, biological cofactors, antibiotics, peptides, proteins, or even whole viruses (Bell et al., *J. Biol. Chem.* 273: 14309-14314, 1998; Gal et al., *Eur. J. Biochem.* 252: 553-562, 1998; Kraus et al., *J. Immunology* 160: 5209-5212, 1998; Yang et al., *Proc. Natl. Acad. Sci. U.S.A.* 95: 5462-5467, 1998; Eaton, *Curr. Opin. Chem. Biol.* 1: 10-16, 1997; Pan et al., *Proc. Natl. Acad. Sci. U.S.A.* 92: 11509-11513, 1995), showing that aptamers can be obtained for almost any desired target whether complex or small. See Famulok and Mayer, *Aptamers as Tools in Molecular Biology and Immunology*, In: *Combinatorial Chemistry in Biology. Current Topics in Microbiology and Immunology* (M. Famulok, C.-H. Wong, E.-L. Winnacker, Eds.), Springer Verlag, Heidelberg, 1999, 123-136 (all references incorporated by reference).

The SELEX process provides a powerful method for the screening of large libraries of oligonucleotides, with diversities of up to $10^{15}$ different molecules, for specific ligand-binding nucleic acids, which in many cases have been shown to not only bind a certain target protein, but also to inhibit its biological function. Such isolated aptamers routinely have high affinity and specificity for their respective targets, and are useful for various therapeutic and/or diagnostic applications. Furthermore, a wide spectrum of chemical modifications of nucleotides is known in the art, which can greatly increase the stability of RNA molecules in biological materials, thus considerably enhancing their application potential.

For example, any potential insufficient stability of the identified nucleic acids as therapeutic agents can easily be overcome by using libraries of chemically modified nucleic acids, such as 2'-fluoro- or 2'-amino-2'-deoxypyrimidine-containing nucleic acids. Such modifications have been shown to be compatible with the enzymatic steps of the SELEX process. Other strategies which circumvent the stability problem of RNA or DNA include the so-called mirror-image, or Spiegelmer, approach by exploiting nuclease resistance of the enantiomer of naturally occurring nucleic acids (KLUβMANN et al., *Nat. Biotechnol.* 14: 1112-1115, 1996; Nolte et al., *Nat. Biotechnol.* 14: 1116-1119, 1996).

Exemplary aptamers that may be used in the instant invention were identified by Williams et al. in 1997 using the SELEX method (Williams et al., *Proc. Natl. Acad. Sci. U.S.A.* 94: 11285-11290, 1997, incorporated by reference), as L-ssDNA ligands to vasopressin. In their approach, D-DNA ligands have been selected using D-vasopressin as a target molecule. The enantiomer of the winning D-ssDNA aptamer, designated as L-ssDNA aptamer, has been synthesized and its ability to bind L-vasopressin was demonstrated Importantly, this approach led to enhanced nuclease stability by mirror-image ssDNA (KLUβMANN et al., *Nat. Biotechnol.* 14: 1112-1115, 1996; Nolte et al., *Nat. Biotechnol.* 14: 1116-1119, 1996). The L-ssDNA-aptamer inhibited cAMP release mediated by vasopressin, but the cAMP release induced by oxytocin was not affected, demonstrating specificity in inhibitory biological activity.

Thus, in one aspect, the subject invention provides a method to identify aptamers that selectively bind pro-VP or fragments thereof, the method comprising contacting a target protein, such as pro-VP, with a library of candidate aptamers, and selectively identifying/isolating/enriching for aptamers that specifically bind the target protein. The identified aptamer may be similarly labeled by moieties including fluorescent dye, radioactive moiety, or a therapeutic agent, as described herein for antibody-based antagonists. Such labeled aptamers can be similarly used in the diagnostic and/or therapeutic applications of the invention, in a similar way the antibody-based pro-VP antagonists are used.

In certain embodiments, the pro-VP antagonist is a scaffold-derived binding protein specific for pro-VP or any of its epitopes.

Engineering scaffold-derived binding proteins that are not members of the immunoglobulin family may possess novel binding functions resembling antibodies. Several classes of protein scaffolds have now been proven to yield reagents with specificities and affinities in a range that was previously considered unique to antibodies. See Skerra, *Current Opinion in Biotechnology*, 18(4): 295-304 (2007) (incorporated by reference). Such engineered protein scaffolds are usually obtained by designing a random library with mutagenesis focused at a loop region or at an otherwise permissible surface area, and by selection of variants against a given target via phage display or related techniques. Several classes of such engineered protein scaffolds have been demonstrated to yield specificities towards different kinds of targets, and to offer practical benefits such as robustness, smaller size, and ease of expression that justify their use as true alternatives to conventional antibodies or their recombinant fragments.

The most promising scaffolds with broader applicability include protein A, the lipocalins, a fibronectin domain, an ankyrin consensus repeat domain, and thioredoxin. Corresponding binding proteins are not only of interest as research reagents or for separation in biotechnology but also as potential biopharmaceuticals, especially in the areas of cancer, autoimmune and infectious diseases as well as for in vivo diagnostics.

Thus, in one aspect, the subject invention provides a method to identify scaffold-derived binding proteins that selectively bind pro-VP or fragments thereof, the method comprising contacting a target protein, such as pro-VP, with a library of candidate scaffold-derived binding proteins, and selectively identifying/isolating/enriching for scaffold-derived binding proteins that specifically bind the target protein. The identified scaffold-derived binding proteins may be similarly labeled by moieties including fluorescent dye, radioactive moiety, or a therapeutic agent, as described herein for antibody-based antagonists. Such labeled scaffold-derived binding proteins can be similarly used in the diagnostic and/or therapeutic applications of the invention, in a similar way the antibody-based pro-VP antagonists are used.

In certain embodiments, the scaffold-derived binding proteins are derived from a scaffold of protein A, a lipocalin, a fibronectin domain, an ankyrin consensus repeat domain, or thioredoxin.

In certain embodiments, the pro-VP antagonist is a fusion protein that functions similarly as an antibody. For example, the anti-Rheumatoid drug etanercept (trade name ENBREL®) treats autoimmune diseases by binding to tumor necrosis factor alpha (TNFα) as a TNFα inhibitor. It is a recombinantly expressed as a fusion protein between the human soluble TNF receptor 2 and the Fc component of human immunoglobulin G1 (IgG1). Such a fusion protein functions similarly as the human-mouse chimeric antibody against TNFα, such as infliximab (trade name REMICADE®).

Thus, any of the above protein based pro-VP antagonists can be made as part of a fusion protein and be used in the methods of the invention. For example, a soluble vasopressin receptor may be fused to the Fc region as in etanercept, and be used as a pro-VP antagonist in the instant invention.

3.4 Linkers

It may be necessary in some instances to introduce an unstructured polypeptide linker region between a label and portions of the antagonist (e.g., antibodies or antigen binding portions). The linker can facilitate enhanced flexibility, and/or reduce steric hindrance between any two fragments. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase a subunit. Other examples of naturally occurring linkers include linkers found in the lcI and LexA proteins.

Within the linker, the amino acid sequence may be varied based on the preferred characteristics of the linker as determined empirically or as revealed by modeling. For instance, in addition to a desired length, modeling studies may show that side groups of certain amino acids may interfere with the biological activity, e.g. DNA binding or transcriptional activation, of the protein. Considerations in choosing a linker include flexibility of the linker, charge of the linker, and presence of some amino acids of the linker in the naturally-occurring subunits. The linker can also be designed such that residues in the linker contact DNA, thereby influencing binding affinity or specificity, or to interact with other proteins. For example, a linker may contain an amino acid sequence which can be recognized by a protease so that the activity of the chimeric protein could be regulated by cleavage. In some cases, particularly when it is necessary to span a longer distance between subunits or when the domains must be held in a particular configuration, the linker may optionally contain an additional folded domain.

In some embodiments it is preferable that the design of a linker involve an arrangement of domains which requires the linker to span a relatively short distance, preferably less than about 10 Angstroms (Å). However, in certain embodiments, depending, e.g., upon the selected domains and the configuration, the linker may span a distance of up to about 50 Angstroms.

Antibodies described herein can be made recombinantly. Linkers may be added to the nucleic acid sequences of the heavy and light chains to increase flexibility of the antibody. In the case of a scFv, the linkers are added to connect the VH and VL chains and the varying composition can effect solubility, proteolytic stability, flexibility, and folding. In one embodiment, a linker of has the amino sequence GSTSG (SEQ ID NO: 7). In another embodiment, a linker has the amino sequence GGSSRSS (SEQ ID NO: 4). Linkers are well-known in the art and can comprise varied amino acid residues depending on the flexibility needed in the resulting recombinant protein to allow for biological activity.

4 Pharmaceutical Compositions

The antagonists (e.g., antibodies and antigen-binding portions) herein can be used, for example, for immuno-based targeting of tumors and delivery of chemotoxic/radiologic agents. Provasopressin-expressing tumors can be localized and imaged using an antibody to the provasopressin protein. Thus, antibodies, antigen-binding portions thereof, and their derivatives could be radiolabeled, conjugated to or used in conjunction with chemotoxic agents, or serve as an attractor for endogenous immune system cells to kill provasopressin-expressing tumors (NRSA/GRSA-expressing tumors). Cancer vaccines may be based on tumor antigens, such as NRSA and GRSA. Because of its unique expression in certain cancers, vaccine strategies based on NRSA/GRSA, such as anti-antibodies or utilizing antigenic motifs on the NRSA/GRSA structure, could be developed that would enable the initial prevention and/or recurrence of these diseases.

4.1 Labels

The antagonists (e.g., antibodies and antigen-binding portions thereof) described herein may be labeled. As used herein, "label" is used to mean a detectable label which is used to visualize the binding of an antibody to its target protein or receptor. Alternatively, antibodies, antigen-binding portions thereof, and peptides may be labeled with, for example, a radiolabel, an iron-related compound, a fluorescent label, or a toxin which would kill or inhibit proliferation of the cell to which it binds. Radiolabels and toxins are well known in the art.

Non-limiting examples of radiolabels include, for example, $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$, $^{121}Sn$, $^{123}I$, $^{125}I$, $^{127}Cs$, $^{128}Ba$, $^{129}Cs$, $^{131}I$, $^{131}C$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$.

Non-limiting examples of toxins include, for example, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Non-limiting examples of fluorescent labels include, for example, FITC, Texas Red, phycoerythrin (PE), cytochrome c, Cy3, and Cy5.

Non-limiting examples of metals such as iron-related compounds include, for example, magnetic iron-oxide particles, ferric or ferrous particles, $Fe_2O_3$, and $Fe_3O_4$. Iron-related compounds and methods of labeling antibodies and polypeptides can be found, for example, in U.S. Pat. Nos. 4,101,435 and 4,452,773, and U.S. published applications 20020064502 and 20020136693, all of which are hereby incorporated by reference in their entirety.

Additionally, other labels, such as biotin followed by streptavidin-alkaline phosphatase (AP), horseradish peroxidase (HRP) are contemplated.

Methodology for labeling proteins, such as antibodies, antigen binding portions thereof, and peptides are well known in the art. When the antibodies, antigen binding portions thereof, and peptides are labeled with a radiolabel or toxin, the antibodies, antigen binding portions thereof, and peptides can be prepared as pharmaceutical compositions which are useful for therapeutic treatment of patients exhibiting increased levels of provasopressin wherein the pharmaceutical compositions are administered to the patient in an effective amount.

In some embodiments, the antibodies, antigen binding portions, or peptides are coupled to a polymer or a functionalized polymer (e.g., a polymer conjugated to another molecule). Examples include water soluble polymers, such as polyglutamic acid or polyaspartic acid, conjugated to a drug such as a chemotherapeutic or antiangiogenic agent, including, for example, paclitaxel or docetaxel.

In certain embodiments, particularly where the cytotoxic moiety is chemically cross-linked to the antibody, antigen binding portion, or peptide moieties, the linkage is hydrolysable, e.g., such as may be provided by use of an amide or ester group in the linking moiety.

In certain embodiments, the subject antibodies, antigen binding portions thereof, or peptides can be coupled with an agent useful in imaging tumors. Such agents include: metals; metal chelators; lanthanides; lanthanide chelators; radiometals; radiometal chelators; positron-emitting nuclei; microbubbles (for ultrasound); liposomes; molecules microencapsulated in liposomes or nanosphere; monocrystalline iron oxide nanocompounds; magnetic resonance imaging contrast agents; light absorbing, reflecting and/or scattering agents; colloidal particles; fluorophores, such as near-infrared fluorophores. In many embodiments, such secondary functionality will be relatively large, e.g., at least 25 amu in size, and in many instances can be at least 50, 100 or 250 amu in size.

In certain preferred embodiments, the secondary functionality is a chelate moiety for chelating a metal, e.g., a chelator for a radiometal or paramagnetic ion. In preferred embodiments, it is a chelator for a radionuclide useful for radiotherapy or imaging procedures.

Radionuclides useful within the compositions and methods herein include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Pb, $^{212}$Bi and $^{213}$Bi. Appropriate therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag, $^{166}$Ho or $^{177}$Lu. As used herein, "radionuclide" and "radiolabel" are interchangeable.

Conditions under which a chelator will coordinate a metal are described, for example, by Gansow et al., U.S. Pat. Nos. 4,831,175, 4,454,106 and 4,472,509 (incorporated by reference).

$^{99m}$Tc is one appropriate radioisotope for diagnostic applications, as it is readily available to all nuclear medicine departments, is inexpensive, gives minimal patient radiation doses, and has good nuclear imaging properties. It has a half-life of six hours which means that rapid targeting of a technetium-labeled antibody is desirable. Accordingly, in certain preferred embodiments, the modified antibodies, antigen binding portions, and peptides include a chelating agent for technetium.

In still other embodiments, the secondary functionality can be a radiosensitizing agent, e.g., a moiety that increases the sensitivity of cells to radiation. Examples of radiosensitizing agents include nitroimidazoles, metronidazole and misonidazole (see: DeVita, V. T. Jr. in Harrison's Principles of Internal Medicine, p. 68, McGraw-Hill Book Co., N.Y. 1983, which is incorporated herein by reference). The modified antibodies, antigen binding portions, and peptides that comprise a radiosensitizing agent as the active moiety are administered and localize at the target cell. Upon exposure of the individual to radiation, the radiosensitizing agent is "excited" and causes the death of the cell.

There are a wide range of moieties which can serve as chelators and which can be derivatized to the antibodies, antigen binding portions, and peptides described herein. For instance, the chelator can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to subject antibodies, antigen binding portions, and peptides. Such groups include, e.g., benzylisothiocyanate, by which the DOTA, DTPA or EDTA can be coupled to, e.g., an amine group.

In one embodiment, the chelate moiety is an "$N_xS_y$" chelate moiety. As defined herein, the term "$N_xS_y$ chelates" includes bifunctional chelators that are capable of coordinately binding a metal or radiometal and, preferably, have $N_2S_2$ or $N_3S$ cores. Exemplary $N_xS_y$ chelates are described, e.g., in Fritzberg et al. (1988) *PNAS* 85:4024-29; and Weber et al. (1990) *Bioconjugate Chem.* 1:431-37; and in the references cited therein.

The Jacobsen et al. PCT application WO 98/12156 provides methods and compositions, i.e., synthetic libraries of binding moieties, for identifying compounds which bind to a metal atom. The approach described in that publication can be used to identify binding moieties which can subsequently be added to antibodies, antigen binding portions, and peptides to derive the modified antibodies, antigen binding portions, and peptides described herein.

Certain of the subject labeled/modified antibodies, antigen binding portions thereof, and peptides can be synthesized, by standard methods known in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively.

Alternatively, base-cleavable linkers, which have been used for the enhanced clearance of the radiolabel from the kidneys, can be used. See, for example, Weber et al. 1990 *Bioconjug. Chem.* 1:431. The coupling of a bifunctional chelate to antibodies, antigen binding portions, and peptides via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysuccinimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hydrazide is used for coupling to the antibodies, antigen binding portions, and peptides, forming an ligand-BFC linkage containing two alkyl ester functions. Such a conjugate is stable at physiological pH, but readily cleaved at basic pH.

Antibodies and antigen binding portions thereof labeled by chelation can be subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, the antibodies and antigen binding portions are coupled to a Boron addend, such as a carborane. For example, carboranes can be prepared with carboxyl functions on pendant side chains, as is well known in the art. Attachment of such carboranes to an amine functionality, e.g., as may be provided on the antibodies, antigen binding portions, and peptides, can be achieved by activation of the carboxyl groups of the carboranes and condensation with the amine group to produce the conjugate. Such modified antibodies, antigen binding portions, and peptides can be used for neutron capture therapy.

The antibodies and antigen-binding portions thereof may also be modified with dyes, for example, useful in photodynamic therapy, and used in conjunction with appropriate non-ionizing radiation. The use of light and porphyrins is also contemplated and their use in cancer therapy has been reviewed by van den Bergh, *Chemistry in Britain*, 22: 430-437 (1986).

One embodiment includes antibodies and antigen binding portions thereof, labeled with a fluorescent label. Common fluorescent labels include, for example, FITC, PE, Texas Red, fluorescent nanodots, rhodamine, and the like. Techniques for labeling polypeptides and proteins are well-known in the art.

One embodiment includes antibodies and antigen binding portions thereof labeled with a metal compound, such as iron, which can be used in MRI imaging and/or for treatment. Iron-containing compounds include both ferrous and ferric-containing compounds, such as ferric-oxides. Specific examples include $Fe_2O_3$ and $Fe_3O_4$. Iron-containing compounds and methods of making iron-coupled antibodies and fragments thereof are described in U.S. Pat. Nos. 4,101,435 and 4,452,773 and published U.S. patent applications 2002/0064502 and 2002/0136693, all of which are hereby incorporated by reference in their entireties.

4.2 Chemotherapeutic Compounds

In certain embodiments, the antibodies and antigen binding portions thereof can be covalently or non-covalently coupled to a cytotoxin, chemotherapeutic agent, or other cell proliferation inhibiting compound, in order to localize delivery of that agent to a tumor cell. For instance, the agent can be selected from the group consisting of alkylating agents, enzyme inhibitors, proliferation inhibitors, lytic agents, DNA or RNA synthesis inhibitors, membrane permeability modifiers, DNA intercalators, metabolites, dichloroethylsulfide derivatives, protein production inhibitors, ribosome inhibitors, inducers of apoptosis, and neurotoxins.

Chemotherapeutics useful as active moieties which when conjugated to antibodies, antigen binding portions, and peptides are specifically delivered to tumorigenic cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication. Examples of known, useful cytotoxic agents are listed, for example, in Goodman et al., *The Pharmacological Basis of Therapeutics*, Sixth Edition, A. G. Gilman et al, eds./Macmillan Publishing Co. New York, 1980 (incorporated by reference). These include taxanes, such as paclitaxel (TAXOL®) and docetaxel (TAXOTERE®); nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used; such drugs are known to those skilled in the art and include puromycin, cycloheximide, and ribonuclease.

Most of the chemotherapeutic agents currently in use in treating cancer possess functional groups that are amenable to chemical cross-linking directly with an amine or carboxyl group of an agent described herein. For example, free amino groups are available on methotrexate, doxorubicin, daunorubicin, cytosinarabinoside, bleomycin, gemcitabine, fludarabine, and cladribine while free carboxylic acid groups are available on methotrexate, melphalan, and chlorambucil. These functional groups, that is free amino and carboxylic acids, are targets for a variety of homobifunctional and heterobifunctional chemical cross-linking agents which can crosslink these drugs directly to a free amino group of an antibody, antigen binding portion thereof, or peptide.

Peptide and polypeptide toxins are also useful as active moieties, and the present disclosure specifically contemplates embodiments wherein the antibodies, antigen binding portions, and peptides are coupled to a toxin. In certain preferred embodiments, the antibodies, antigen binding portions, or peptides and the toxin are both polypeptides and are provided in the form of a fusion protein. Peptide and polypeptide toxins are generally complex toxic products of various organisms including bacteria, plants, etc. Examples of toxins include but are not limited to: ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

Chemotherapeutic agents include chemotherapeutic drugs that are commercially available.

Merely to illustrate, the chemotherapeutic can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes—dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. Preferred dosages of the chemotherapeutic agents are consistent with currently prescribed dosages.

4.3 Amino Acid Analogs

In certain embodiments, an antibody or antigen-binding portion thereof as described herein may comprise one or more amino acid analogs, derivatives and congeners of any specific amino acid referred to herein, as well as C-terminal or N-terminal protected amino acid derivatives (e.g. modified with an N-terminal or C-terminal protecting group). For example, one may use an amino acid analog wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and may be used according to the disclosures herein.

4.4 Combinations of Provasopressin Antibodies and Abnormal Vasopressin $V_2$ Receptor Antibodies In some embodiments, the antibodies and antigen-binding portions thereof may be co-administered with antibodies immunoreactive with the vasopressin abnormal V2 receptor. Due to a splicing error, cancer cells often produce an abnormal form of the V2 receptor, which is a good tumor cell marker for targeted therapy.

4.5 Pharmaceutical Additives

In certain embodiments, the antagonists (e.g., antibodies or antigen-binding portions thereof) are formulated with a pharmaceutically acceptable carrier. The antibodies or antibody variants can be administered alone or as a component of a pharmaceutical formulation (composition). They may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The subject formulations include those suitable for oral, dietary, topical, parenteral (e.g., intravenous, intraarterial, intramuscular, subcutaneous injection), inhalation (e.g., intrabronchial, intranasal or oral inhalation, intranasal drops), rectal, and/or intravaginal administration. Other suitable methods of administration can also include rechargeable or biodegradable devices and slow release devices such as slow release polymeric devices. The pharmaceutical compositions can also be administered as part of a combinatorial therapy with other agents (either in the same formulation or in a separate formulation).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

In certain embodiments, methods of preparing these formulations or compositions include combining another type of anti-cancer therapeutic agent and a carrier and, optionally, one or more accessory ingredients. In general, the formulations can be prepared with a liquid carrier, or a finely divided solid carrier, or both, and then, if necessary, shaping the product.

Pharmaceutical compositions suitable for parenteral administration may comprise one or more antibodies, antigen-binding portions thereof, or peptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In some embodiments, the antibodies or antigen-binding portions are formulated with pharmaceutically acceptable carriers. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Injectable depot forms are made by forming microencapsule matrices of one or more antibodies in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, polymeric nanoparticles, or microemulsions which are compatible with body tissue.

In certain embodiments, the pharmaceutical composition is administered by subcutaneous, intravenous, intranasal, parenteral, transdermal, intracheal, intravenous, intramuscular, intracranial, intrathecal or intravitreal injection; by oral administration, eye drops, pessary, or inhalation.

To achieve the desired effects, the antibodies, antigen-binding portions thereof, or peptides can be administered in a variety of unit dosage forms. The dose will vary according to the particular antibody or antigen-binding portion thereof. For example, different antibodies may have different masses and/or affinities, and thus require different dosage levels. Antibodies prepared as Fab' fragments will also require differing dosages than the equivalent intact immunoglobulins, as they are of considerably smaller mass than intact immunoglobulins, and thus require lower dosages to reach the same molar levels in the patient's blood.

The dose will also vary depending on the manner of administration, the particular symptoms of the patient being treated, the overall health, condition, size, and age of the patient, and the judgment of the prescribing physician. Dosage levels of the antibodies for human subjects are generally between about 1 mg per kg and about 100 mg per kg per patient per treatment, and preferably between about 5 mg per kg and about 50 mg per kg per patient per treatment. In terms of plasma concentrations, the antibody concentrations are preferably in the range from about 5-1000 µg/ml, preferably 25 µg/ml to about 500 µg/ml.

Subject to the judgment of the physician, a typical therapeutic treatment includes a series of doses, which will usually be administered concurrently with the monitoring of clinical endpoints (such as tumor load or presence of provasopressin fragments in the bloodstream) with the dosage levels adjusted as needed to achieve the desired clinical outcome. Other protocols can, of course, be used if desired as determined by the physician.

Administration of the compositions described herein may be performed by an intravascular route, e.g., via intravenous infusion by injection. Other routes of administration may be used if desired, such as s.c. injection. Formulations suitable for injection are found in Remington's Pharmaceutical Sciences, Mack Publishing Company, Philadelphia, Pa., 17th ed. (1985). Such formulations must be sterile and non-pyrogenic, and generally will include a pharmaceutically effective carrier, such as saline, buffered (e.g., phosphate buffered) saline, Hank's solution, Ringer's solution, dextrose/saline, glucose solutions, and the like. The formulations may contain pharmaceutically acceptable auxiliary substances as required, such as, tonicity adjusting agents, wetting agents, bactericidal agents, preservatives, stabilizers, etc.

5: Diagnostic Methods

Applicants provide, inter alia, a rapid, inexpensive, sensitive, and specific method for: 1) early detection of cancer; and 2) identifying and localizing provasopressin-expressing cancers, including metastatic and/or recurrent disease, in patients. Cancers that may be imaged using the methods herein include carcinoid tumors and pancreatic endocrine tumors, and others discussed in section 7 of this application.

In this respect it should be useful to all hospitals and physicians examining and treating patients with provasopressin-expressing cancers. Detection kits are simple enough to be set up in any local hospital laboratory, and anti-provasopressin antibodies and antigen-binding portions thereof can readily be made available to all hospitals treating patients with breast cancer.

5.1. Methods of Phenotyping Cancer Samples.

The instant disclosure also provides a method of phenotyping biological samples from patients having a provasopressin-expressing cancer other than breast cancer or small cell lung cancer comprising: (a) obtaining a biological sample from a patient; (b) (optionally) rendering the biological sample amenable to immunoassay; (c) contacting the rendered sample with the a provasopressin-binding antibody or antigen-binding portion thereof under conditions that allow for binding of the antibody or antigen-binding portion to provasopressin; and (d) determining if the cells of the rendered sample inappropriately express provasopressin compared to a control tissue; wherein if the test tissue inappropriately expresses provasopressin, the biological sample is identified as likely having cancerous cells. In some embodiments, if the test tissue shows inappropriate provasopressin expression, one may administer a therapeutically effective amount of a provasopressin-binding antibody or antigen-binding portion thereof to the patient. In some embodiments, before step (a), the patient has been diagnosed as having a provasopressin-expressing cancer such as prostate cancer, pancreatic cancer, or neuroendocrine cancer.

5.2 Methods of Phenotyping Blood Samples for Non-invasive or Less-invasive Cancer Detection.

Certain tumors may be detected by measuring blood levels of provasopressin components. This may be done with anti-provasopressin antibodies, antigen-binding portions thereof. Such antibodies include, for example, MAG-1, MAG-2, MAG-3, MAG-4, and MAG-5, and any of the derivative antibodies and antigen-binding portions thereof referred to herein. These antibodies and antigen-binding portions thereof would be useful in the clinical screening assay to measure provasopressin (or fragments of provasopressin) levels in the blood of patients suspected of having provasopressin-expressing tumors (such as neuroendocrine, pancreatic, or prostate tumors), or who have had those tumors in the past. This would be a useful, non-invasive or less invasive test to possibly justify further, more invasive tests/biopsies, and aid in monitoring recurrence of disease.

5.3 In Vivo Diagnostic Techniques

Herein Applicants disclose, among other things, a method of detecting a tumor in a patient having a provasopressin-expressing cancer other than breast cancer or small cell lung cancer comprising: (a) administering a pharmaceutical composition comprising a provasopressin-binding antibody or antigen-binding portion thereof to the patient, (b) detecting the label, and (c) determining if the patient has cells that inappropriately express provasopressin compared to a control; wherein if the patient has cells that inappropriately express provasopressin, the patient is identified as likely having a tumor. In certain embodiments, the method further comprises, if the patient has cells that inappropriately express provasopressin, administering a therapeutically effective amount of a provasopressin-binding antibody or antigen-binding portion thereof to the patient. In certain embodiments, before step (a), the patient has been diagnosed as having a provasopressin-expressing cancer. The method may further comprise determining the location and/or volume of a plurality cells inappropriately expressing provasopressin (for example, determining the volume of a tumor). This method may be used to determine the location of a tumor prior to surgical resection of the tumor. It may also be used to determine whether surgery is appropriate.

With the use of antagonists (e.g., antibodies) directed against various portions NRSA/GRSA, current imaging techniques, such as MRI, could be greatly enhanced, and new imaging protocols for diseases such as pancreatic and prostate cancer could be developed and effectively implemented for clinical use. These types of techniques would be especially useful for the detection of metastatic disease. These techniques could also assist a surgeon preparing to surgically remove a tumor or tumors, by identifying the location of the tumor or tumors.

6. Therapeutic Methods 6.1 Methods of Therapy with Anti Provasopressin Antibodies Herein Applicants disclose, inter alia, a method of treating a provasopressin-expressing cancer, comprising administering an effective amount of the pharmaceutical compositions described herein to a subject. These pharmaceutical compositions include anti-provasopressin antibodies (such as MAG-1, MAG-2, MAG-3, MAG-4, and MAG-5 or any of the variants described herein), and antigen-binding portions thereof.

In certain embodiments, an antibody (or antigen-binding portion thereof) suitable for therapeutic use is a humanized antibody or antigen-binding portion thereof. The antibodies and antigen-binding portions may be humanized by any means known in the art, such as CDR grafting or generation of a chimeric antibody. Specific point mutations may also be made during the humanization process.

Antibodies can be used for targeting provasopressin (NRSA/GRSA) on certain tumors. It was shown previously that SCLC tumors can be localized and imaged in humans using radiolabeled antibody directed against the neurophysin portion of provasopressin. Subsequent studies show that polyclonal antibodies, monoclonal antibodies, and antibody Fab fragments directed against different regions of the provasopressin protein bind specifically to cultured SCLC and breast cancer cells, as well as to human tumor sections, but not to tissue that is devoid of tumor.

Described herein are polyclonal and monoclonal antibodies, and their Fab fragment derivatives, to NRSA/GRSA. It has been shown here that these antibodies and fragments can bind to cultured human cancer cells and human cancer tissue other than that of SCLC and breast cancer. Since the NRSA/GRSA is not typically found in normal cells, it can serve as an excellent target for tumor localization in the early detection, diagnosis, and treatment of cancers that express the vasopressin gene. NRSA/GRSA also provides for a attractive candidate for use in vaccine development strategies for the prevention of those cancers that express the vasopressin gene.

Single-chain antibodies fragments and small binding peptides can be used for targeting provasopressin (NRSA/GRSA) on tumors. We also disclose single-chain variable region fragments (scFv) antibodies that bind to NRSA/GRSA. The use of such smaller molecules will provide added benefits (tumor penetration, ease of manufacturing) for in vivo tumor targeting.

An effective therapeutic response is achieved when the patient experiences partial or total alleviation or reduction of signs or symptoms of illness, and specifically includes, without limitation, prolongation of survival. In certain embodiments, a therapeutic response is achieved when the patient's symptoms remain static, and the tumor burden does not increase.

6.2 Methods of Combination Therapy

Herein Applicants disclose, inter alia, a method of treating provasopressin-expressing cancers, comprising administering an effective amount of a pharmaceutical composition comprising an anti-provasopressin antibody (such as MAG-1, MAG-2, MAG-3, MAG-4, and MAG-5 or any of the variants described herein), or an antigen-binding portion thereof to a subject, and further comprising administration of a second treatment. The second treatment may be surgery, radiation therapy, or an effective amount of a second pharmaceutical composition. The second pharmaceutical compositions may comprise a chemotherapeutic agent, and optionally comprising epinephrine. The pharmaceutical compositions may be administered concomitantly, in a single formulation, or in separate formulations. Alternatively, the second pharmaceutical composition may comprise one or more of dexamethasone, IBMX, and 8-bromoadenosine 3',5'-cyclic monophosphate (8br-cAMP). In one embodiment, the second pharmaceutical composition comprises each of dexamethasone, IBMX, and 8-bromoadenosine 3',5'-cyclic monophosphate (8br-cAMP). Alternatively, the second pharmaceutical composition may comprise one or more of IBMX and forskolin. In one embodiment, the second pharmaceutical composition comprises both of IBMX and forskolin.

Provasopressin-binding antibodies and antigen binding portions can be used in combination therapy with chemotherapeutic agents. As described herein, provasopressin-binding antibodies and antigen-binding portions thereof in combination with a cocktail of chemotherapeutic agents are effective at inhibiting proliferation of cancerous cells when administered in an effective amount.

Treatment for the various representative cancers, including chemotherapy using chemnotherapeutic agents, are described in more detail below for the representative cancers. All such treatments may be used in combination with treatment with the subject provasopressin-binding agents.

The above listed agents are merely for illustrative purpose only. One of ordinary skill in the art could prepare a formulation of any of the chemotherapeutic agents as described above to be administered with a preparation of one of the disclosed antibodies or antigen-binding portions thereof to treat a provasopressin-expressing cancer.

7. Treatable Diseases

Using the methods described herein, one may treat a patient with a provasopressin-expressing cancer. Examples of provasopressin-expressing cancers include neuroendocrine cancers, prostate cancer, and pancreatic cancer. In certain embodiments, the provasopressin-expressing cancer is not SCLC and breast cancer.

7.1 Neuroendocrine Tumors

Many neuroendocrine tumors are either carcinoid tumors or pancreatic endocrine tumors (PETs). In certain embodiments, the neuroendocrine tumor is a pancreatic tumor that is not an adenopancreatic cancer or exocrine pancreatic cancer. A neuroendocrine tumor may be, for example, an insulinoma, a gastrinoma, a glucagonoma, a VIPoma, a PPoma, a somatostatinoma, a CHRoma, a calcitoninoma, a GHRHoma, a neurotensinoma, a ACTHoma, a GRFoma, a GRFoma, a parathyroid hormone-related peptide tumor, or a WDHA. Carcinoid tumors may arise from several points of origin, including the foregut (lung, thymus, stomach, and duodenum), midgut (distal ileum and proximal colon), or hindgut (distal colon and rectum). Some carcinoid tumors produce serotonin. Neuroendocrine cancers may be brain, gastroenteric, ovarian, testicular, adrenal, or skin cancers.

Certain methods of diagnosing neuroendocrine cancers are known in the art. For example, MRI, blood tests to determine hormone levels, CT scans, sonography, and endoscopy may be used to diagnose neuroendocrine cancers. Also, a number of biomarkers for neuroendocrine cancers are known, including chromogranin A, urine 5-hydroxy indole acetic acid, neuron-specific enolase, and synaptophysin. The diagnostic techniques provided herein may be used in concert with any other technique for diagnosing neuroendocrine cancer.

Known methods of treating neuroendocrine cancers include the administration of somatostatin analogues such as octreotide (marketed as Sandostatin). Sometimes, the somatostatin analogue is conjugated to a radionuclide such as indium-111, lutetium-177, or yttrium-90. Chemotherapy, surgery, and radiation therapy may also be used to treat neuroendocrine cancers. In some cases, a chemotherapeutic agent is delivered to the hepatic artery to target neuroendocrine tumors in the liver. Radiofrequency ablation and cryoablation are other techniques used in the therapy of neuroendocrine cancers. Other treatments include neovascularization inhibitors, epidermal growth factor receptor (EGFR) inhibitors, vascular endothelial growth factor receptors (VEGFR) inhibitors, and angiopoietin-related growth factor (AGF) inhibitors. Treatments of neuroendocrine cancers include interferons, cisplatin, etoposide, doxorubicin, streptozocin, everolimus (Afinitor), imatinib, sunitinib (Sutent), temozolide, thalidomide, sorafenib, and panitumumab. Therapy with a provasopressin-binding antibody or antigen-binding portion thereof may be combined with any of the above therapies.

7.2 Pancreatic Cancers

Pancreatic cancer includes pancreatic carcinomas, sarcomas, and melanomas. These may occur in poorly differentiated, moderately differentiated, and well differentiated forms. Some pancreatic cancers are neuroendocrine cancers. Others are adenopancreatic cancers. Pancreatic cancers include endocrine and exocrine pancreatic cancer. Pancreatic tumors can be benign or malignant.

A number of methods of diagnosing pancreatic cancers are known in the art. For example, a patient may present with one or more of pain, jaundice, weight loss, loss of appetite. Imagine techniques such as CT scans, MRI, and endoscopic ultrasound can be used to identify a pancreatic tumor. The diagnostic techniques provided herein may be used in concert with any other technique for diagnosing pancreatic cancer.

Previously known methods of treating pancreatic cancer include surgery, radiation therapy, chemotherapy, chemoradiation therapy, and cancer vaccines. Appropriate chemotherapeutic agents include gemcitabine (Gemcitabine Hydrochloride), Gemzar (Gemcitabine Hydrochloride), oxaliplatin, Fluorouracil (5FU), Adrucil (Fluorouracil), Efudex (Fluorouracil), Fluoroplex (Fluorouracil), Mitomycin C, Mitozytrex (Mitomycin C), Mutamycin (Mitomycin C), or Erlotinib Hydrochloride (Tarceva).

Another treatment for pancreatic cancer is the monoclonal antibody Denosumab. The therapeutic techniques provided herein may be used in concert with any other technique for treating pancreatic cancer.

7.3 Prostate Cancers

Types of prostate cancer include neuroendocrine prostate cancer, sarcomas, small cell carcinomas, transitional cell carcinomas, and prostate adenocarcinomas. Prostate cancer may be classified into four stages, T1, T2, T3, and T4. Prostate tumors can be benign or malignant.

Prostate cancer can be identified by screening for elevated levels of PSA. Diagnosis can also involve imaging techniques such as transrectal ultrasound. Biopsies, such as needle biopsies, are another common diagnostic technique. The diagnostic techniques provided herein may be used in concert with any other technique for diagnosing prostate cancer.

Prostate cancer can be treated by, for example, surgery, radiation therapy, cancer vaccines, proton therapy, cryotherapy, hormonal therapy, high intensity focused ultrasound, proton beam radiation therapy, and chemotherapy. Androgen ablation is a common treatment, and can involve surgical removal of the testicles, administration of female sex hormones, and treatment with antiandrogens (such as finasteride). Chemotherapeutic agents used to treat prostate cancer include docetaxel (Taxotere), doxorubicin (Adriamycin), estramustine phosphate (Emcyt), etoposide (Vepsid), mitoxantrone (Novantrone), paclitaxel (Taxol), vinblastine (Velban), Cabazitaxel, Degarelix, Docetaxel, Enzalutamide Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Provenge (Sipuleucel-T), Sipuleucel-T, Taxotere (Docetaxel), Viadur (Leuprolide Acetate), Xtandi (Enzalutamide), and, Zytiga (Abiraterone Acetate).

The therapeutic techniques provided herein may be used in concert with any other technique for treating prostate cancer.

8 Kits

One embodiment includes for a kit useful for screening a biological sample for a provasopressin-expressing cancer and for identifying/selecting patients (form which the sample is derived from) for treatment, the kit comprising a preparation of an antibody or antigen binding portion immunoreactive with provasopressin or fragment of provasopressin, wherein the antibody immunoreactive with provasopressin indicates the presence of a provasopressin-expressing cancer. The kit may be labeled for use in detecting provasopressin-expressing tumors. The fragment of provasopressin may be, for example, SEQ ID NOs: 1, 5, or 6. If the biological sample is positive for provasopressin, a provasopressin-expressing cancer has been identified.

One embodiment of the kits include preparations of antibodies or antigen binding portions immunoreactive with provasopressin or fragment of provasopressin. Antibodies and antigen binding portions can be lyophilized or in solution. Additionally, the preparations can contain stabilizers to increase the shelf-life of the kits, e.g., bovine serum albumin (BSA). Wherein the antibodies and antigen binding portions are lyophilized, the kit can contain further preparations of solutions to reconstitute the preparations. Acceptable solutions are well known in the art, e.g., PBS.

Kits can further include the components for an ELISA assay for measuring provasopressin and fragments thereof as tumor markers in body fluids. Samples to be tested in this application include, for example, plasma, urine, lymph, breast ductal secretions and products thereof. Alternatively, preparations of the kits may be used in immunoassays, such as immunohistochemistry to test patient tissue biopsy sections.

The compositions of the kit can be formulated in single or multiple units for either a single test or multiple tests. In certain embodiments, the preparations of the kit are free of pyrogens. The kits can include instructions for the use of the compositions in an immunoassay.

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, *Molecular Cloning: A Laboratory Manual*, 3rd Ed., ed. by Sambrook and Russell (Cold Spring Harbor Laboratory Press: 2001); the treatise, Methods In Enzymology (Academic Press, Inc., N.Y.); *Using Antibodies*, Second Edition by Harlow and Lane, Cold Spring Harbor Press, New York, 1999; *Current Protocols in Cell Biology*, ed. by Bonifacino, Dasso, Lippincott-Schwartz, Harford, and Yamada, John Wiley and Sons, Inc., New York, 1999; *DNA Cloning*, volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D Hames & S. J. Higgins eds. 1984); *Transcription and Translation* (B. D. Hames & S. J. Higgins eds. 1984); and *Current Protocols in Immunology, Molecular Biology, Cell Biology, Human Genetics, Protein Science, and Nucleic Acid Chemistry* (John Wiley & Sons, Inc., Edison, N.J.).

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

The present invention is illustrated by the following examples which should not be construed as limiting in any way. The contents of all cited references (including literature references, issued patents, published patent applications as cited throughout this application) are hereby expressly incorporated by reference.

Materials and Methods

Cultured Cell Lines and Human Tissues

Cultured cells were grown in DMEM/F12 (50:50) medium supplemented with 10% Fetal calf serum, 2 mM glutamine, 100 units/mL penicillin and 100 µg/mL streptomycin at 37° C. and 5% $CO_2$. Table 1 is a list of representative cancer cell lines used for the studies. These cells are available at American Type Culture Collection (ATCC) (Manassas, Va.). Human normal and tumor tissue samples were obtained commercially or from the Pathology Department of Dartmouth Medical School. Human hypothalamus tissue was obtained at autopsy with the assistance of Dr. C. Harker Rhodes (Dartmouth Medical School).

TABLE 1

Representative Cancer Cell Lines

| Cancer | Cell Line |
|---|---|
| Breast Cancer | MCF-7, MDA-MB231, SKBr3 |
| Pancreatic Cancer | Bxpc3, Panc1-1 |
| Prostate | PC3, DUI145 |
| Ovarian Cancer | SKOV3, OVA2780, OV2008 |
| Testicular Cancer | NT2-D1 |

Monoclonal Antibodies and Fab Fragments

All procedures involving animals were conducted with the approval of the American Association for the Accreditation of Laboratory Animal Care (AAALAC) certified Dartmouth College and Dartmouth Hitchcock Medical Center Institutional Animal Care and Use Committee (IACUC).

MAG-1 mAb was generated against a synthetic 18-amino acid peptide representing the COOH-terminal VAG region of the pro-VP protein (VAGc18: VQLAGAPEPFEPAQP-DAY; SEQ ID NO: 5) coupled to bovine thyroglobulin using glutaraldehyde. This complex was used as a 1 mg/mL solution (peptide equivalent concentration) in 0.05 M sodium phosphate (pH 7.0) that had been sonicated with an equal volume of complete Fruend's adjuvant (CFA) to immunize BALB/c mice. A follow-up immunization was performed 21 days later using an mixture of antigen with incomplete Freund's adjuvant (IFA), and spleen cells were harvested after an additional five days.

The spleen cells were hybridized with Sp2/0-Ag14 cells, and viable hybridomas were selected using DMEM containing 10% FBS and supplemented with hypoxanthine-aminopterin-thymidine (HAT) (Sigma). Clones were screened for the production of antibodies using $^{125}$I-VAGc18 peptide by displacement RIA (North et al. (1978) Endocrinology, 103: 1976-1984). The MAG-1-producing clone was isolated, used to generate MAG-1 monoclonal antibody, which was purified by a Protein A column.

MAG-1 was determined to be of isotype $IgG_1$ using a Clonotyping System kit (Southern Biotechnology Associates, Birmingham, Ala.). Fab fragments of MAG-1 were generated using an ImmunoPure $IgG_1$ Fab and $F(ab)_2$ Preparation Kit (Pierce, Rockford, Ill.) following the manufacturer's instructions, and complete ficin digestion of the IgG molecule was confirmed by Western analysis.

Chimeric and humanized MAG-1 antibody were generated after the cloning of the heavy and light chain of the murine MAG-1 antibody by conventional means as described in the literature. Both chimeric and humanized MAG-1 were cloned and expressed in Chinese Hamster Cells (CHO).

This or similar procedures may be used (optionally with minor modifications) to produce other antibodies with similar binding property as that of MAG-1. For example, four additional similar antibodies (MAG-2, -3, -4, and -5) were produced using similar procedures. See Example 1 of WO2009/137113A2 (incorporated by reference). The hybridomas used to produce MAG-1 to MAG-5 are 8D12A4, 8D12A12, 4E5A5, 4E5A11, AND 8C10A11, respectively. These monoclonal antibodies all bind to the VAGc18 antigen used to raise the antibodies, but all fail to bind to a related peptide produced by replacing the $9^{th}$ Pro in the VAGc18 sequence with His. In addition, the MAG-1 related antibodies all behave similarly in competitive inhibition binding studies, and their $K_d$ are all within 10-fold of one another (e.g., for MAG-1 to MAG-5, $1.5\times10^{-8}$ M, $1.5\times10^{-8}$ M, $2.7\times10^{-8}$ M, $3.25\times10^{-9}$ M, and $3.41\times10^{-9}$ M, respectively, concerning binding to the VAGc18 antigen), demonstrating the reliability of the antibody production method. See WO2009/137113A2 (incorporated by reference) for further characterization.

Reverse-Transcriptase Polymerase Chain Reaction (RT-PCR) of the Pro-VP Protein

Total RNA was isolated from cultured cells or human tissues using Trizol (Life Technologies, Inc., Rockville, Md.), and 1 μg was used together with oligo(dT) primers and RNase $H^-$ reverse transcriptase (Life Technologies, Inc.) in a standard reverse transcription reaction following the manufacture's instructions. Polymerase chain reaction (PCR) was performed using primers AVPfwd (5'-aggatgcctgacaccatgctg-3'; SEQ ID NO: 8) and AVPrev (5'-attggcggaggtttattgtc-3'; SEQ ID NO: 9) in a reaction employing MasterTaq enzyme, TagMaster PCR Enhancer buffer, and a Mastercycler Gradient thermocycler (Eppendorf, Westbury, N.Y.). These primers were designed to span the 2 introns of the VP gene and amplify the entire coding sequence of the pro-VP protein. Cycle conditions were as follows: 1× (95° C. for 5 min), 4× (95° C. for 1 min, 62° C. for 1 min minus 1° C. per cycle, 72° C. for 1 min), 30× (95° C. for 1 min, 57° C. for 1 min, 72° C. for 1 min) followed by a final extension at 72° C. for 10 min.

Reverse-Transcriptase Polymerase Chain Reaction (RT-PCR) of Antibody Fragments

Total RNA was isolated from cultured cells or human tissues using Trizol (Life Technologies, Inc., Rockville, Md.), and 1 μg was used together with oligo(dT) primers and RNase $H^-$ reverse transcriptase (Life Technologies, Inc.) in a standard reverse transcription reaction following the manufacture's instructions.

Polymerase chain reaction (PCR) was performed using primers Vh fwd: (5'-AGGTSMARCTGCAGSAGTCWGG-3'; SEQ ID NO: 14); Vh rev: (5'-CCAGGGGCCAGTGGATAGACAAGCTTGGGTGTCGTTTT-3'; SEQ ID NO: 15); V1 fwd: (5'-GGTGATATCWTGMTGACCCAAWCTCCACTCTC-3'; SEQ ID NO: 16); and V1 rev: (5'-GGGAAGATGGATCCAGTTGGTGCAGCATCAGC-3'; SEQ ID NO: 17); in a reaction employing MasterTaq enzyme, TagMaster PCR Enhancer buffer, and a Mastercycler Gradient thermocycler (Eppendorf, Westbury, N.Y.). These primers were designed to span the IgG antibody Fv-DNA and amplify the entire coding sequence of the IgG antibody Fv-DNA. Cycle conditions were as follows: Initial denaturation of 94° C. for 5 minutes; 35 cycles (1 min at 94° C., 2 min at 52° C., 2 min at 72° C.), followed by a final extension at 72° C. for 10 minutes.

Primers were developed based on the MAG-1 sequence with a Sfi1 restriction site for insertion into the pComb3× vector (The Scripps Research Institute, La Jolla, Calif.). Primers used in the PCR reaction for the Vh-Vl orientation are as follows: Vh-fwd: (5'-GGGCCCAGGCGGCCGAGGTCAAGCTGCAGGAGTCA-3'; SEQ ID NO: 18); Vl-rev: (5'-CCTGGCCGGCCTGGCCTTTKATTTCCAGYTTGGTCCC-3'; SEQ ID NO: 19); Vh rev: (5'-ACCGGAAGTAGAGCCGGAGACTGTGAGAGTGGAGCC-3'; SEQ ID NO: 20); and V1 fwd: (5'-GGCTCTACTTCCGGTGATATCGTTATGACCCCAACT-3'; SEQ ID NO: 21). PCR conditions were as follows: initial denaturation of 94° C. for 5 minutes; 35 cycles (30 sec at 90° C., 30 sec at 52° C., 90 sec at 72° C.); followed by a final extension at 72° C. for 10 minutes.

Primers used in the PCR reaction for the Vl-Vh orientation are as follows: Vl-fwd: (5'-GGGCCCAGGCGGCCGAGCTCGAYATCCAGCTGACTCAGCC-3'; SEQ ID NO: 10); Vh-rev: (5'-CCTGGCCGGCCTGGCCACTAGTGACAGATGGGGSTGTYGTTTTGG-3'; SEQ ID NO: 11); Vl-rev: (5'-GGAAGATCTAGAGGAACCACCTTTKATTTCCAGYTTGGTCCC-3'; SEQ ID NO: 12); and Vh-fwd: (5'-GGTGGTTCCTCTAGATCTTCCCTCGAGGTRMAGCTTCAGGAGTC-3'; SEQ ID NO: 13). PCR conditions were as follows: initial denaturation of 94° C. for 5 minutes; 35 cycles (30 sec at 90° C., 30 sec at 56° C., 90 sec at 72° C.); followed by a final extension at 72° C. for 10 minutes.

For the above primers, the degenerate primers are as follows: K=G or T; R=A or G; Y=C or T; S=G or C; M=A or C; and W=A or T.

Confocal Microscopy

Approximately 10,000 to 20,000 cancer cells in 70 μL were seeded onto a cover slip in a 60 mm petri dish with cover and incubated overnight at 37° C. in a 5% $CO_2$ incubation. The cells were fixe with Formalin for 15 minutes at room temperature. The cells were then washed thrice with phosphate buffered saline containing calcium and magnesium ions (PBS). The liquid was removed and 1 drop of phosphate buffered gelatin was added and the cells were incubated at room temperature for an hour. The cells were then washed again thrice with PBS. The fluid was aspirated and 50 μl of MAG-1, the primary antibody at a concentration of 10 µg/ml were then added to the cells and incubated at room temperature for an hour. The cells were then washed thrice with PBS. 50 µL of goat anti-mouse Fab-FITC at a 1:2000 dilution were added and incubated at room temperature for 1 hr. The stained cells were then visualized by confocal microscopy, using a confocal microscope. When chimeric or humanized MAG-1 was used for staining as the primary antibody, goat anti-human heavy and light chain was used as at the secondary antibody. For control, MOPC-21 was used as the primary antibody. Alternatively, to demonstrate specific binding, the MAG-1 was incubated with the C18 peptide used to raise the monoclonal antibody before adding to the cancer cells on the cover slip.

Immunohistochemistry

Sections of 4-6 µm from each formalin-fixed, or acetone-fixed, paraffin-embedded specimens of human SCLC, normal lung, or hypothalamus tissue were stained for NRSA with MAG-1 mAb. Fixed preparations of breast cancer, DCIS, fibrocystic disease, or normal breast tissue were stained for GRSA with MAG-1. All steps were performed at ambient temperature unless otherwise stated. The sections were deparaffinized by heat exposure (60° C. for 2 h) followed by xylene washes (2×10 min), and tissues were re-hydrated by washes (10 min) in descending concentrations of ethanol (100%-70%). Endogenous peroxide activity was blocked by incubation in 0.6% hydrogen peroxidase in methanol for 10 min After washing with PBS (2×3 min), the tissues were subjected to antigen retrieval by proteolytic digestion with trypsin solution (BioGenex, San Ramon, CA) for 10 min at 37° C., washed in 95% ethanol for one minute, and then in PBS for 10 min. Slides were blocked with Power Block Universal Blocking Reagent (BioGenex) for 20 min and incubated with MAG-1 mAb (0.25 µg/ml) in PBS with 0.1% BSA overnight at 4° C. Following washes with PBS (2×3 min), the slides were incubated with MultiLink biotinylated goat anti-immunoglobulins solution (BioGenex) for 20 minutes, washed with PBS (2×3 min), and incubated with Label peroxidase-conjugated streptavidin solution (BioGenex) for 20 min After washing, staining was achieved using 3,3'-diaminobenzidine (DAB) substrate solution (BioGenex) for 2-5 minutes. Tissues were then counterstained with hematoxylin, dehydrated in ascending concentrations of ethanol, washed in xylene, and cover-slipped using SuperMount mounting medium (BioGenex).

Alternatively, sections of 4-6 µm from each formalin-fixed paraffin-embedded specimens of human SCLC, normal lung, or hypothalamus tissue were stained for NRSA with MAG-1 mAb. All steps were performed at ambient temperature unless otherwise stated. The sections were deparaffinized by heat exposure to (60° C. for 10 min) followed by xylene washes (2×5 min), and tissues were re-hydrated by washes (2×5 min) in descending concentrations of ethanol (100%, 95%, and 70%). After washing with PBS (2×5 min), the tissues were subjected to antigen retrieval by 0.01 M sodium citrate (pH 8.5) for 30 min at 80° C. Slides were washed in PBS (2×5 min) and then incubated in Power Block Universal Blocking Reagent (BioGenex) for 5 min and incubated with MAG-1 mAb (1 µg/ml) in PBS with 0.1% BSA and 0.02% Tween 20 and reacted with the tissue sections for 1 h. After washes with PBS (3×5 min), the slides were incubated with MultiLink biotinylated goat anti-immunoglobulins solution (BioGenex) for 30 minutes, washed with PBS (3×5 min), and incubated with Label peroxidase-conjugated streptavidin solution (BioGenex) for 30 min After washing in PBS (3×5 min), staining was achieved using 3,3'-diaminobenzidine (DAB) substrate solution (BioGenex) for 3 minutes. Tissues were then counterstained with hematoxylin, dehydrated in ascending concentrations of ethanol, washed in xylene, and cover-slipped using SuperMount mounting medium (BioGenex).

EXAMPLE I

Detection of NRSA in SCLC Tumor Tissue and Cultured Cells

Total RNA was extracted from human lung SCLC tumor and non-tumor tissue samples and analyzed for the presence of the vasopressin message by RT-PCR. The PCR reaction was carried out with sequence-specific primers that spanned the two introns of the vasopressin gene.

Figure 2A:
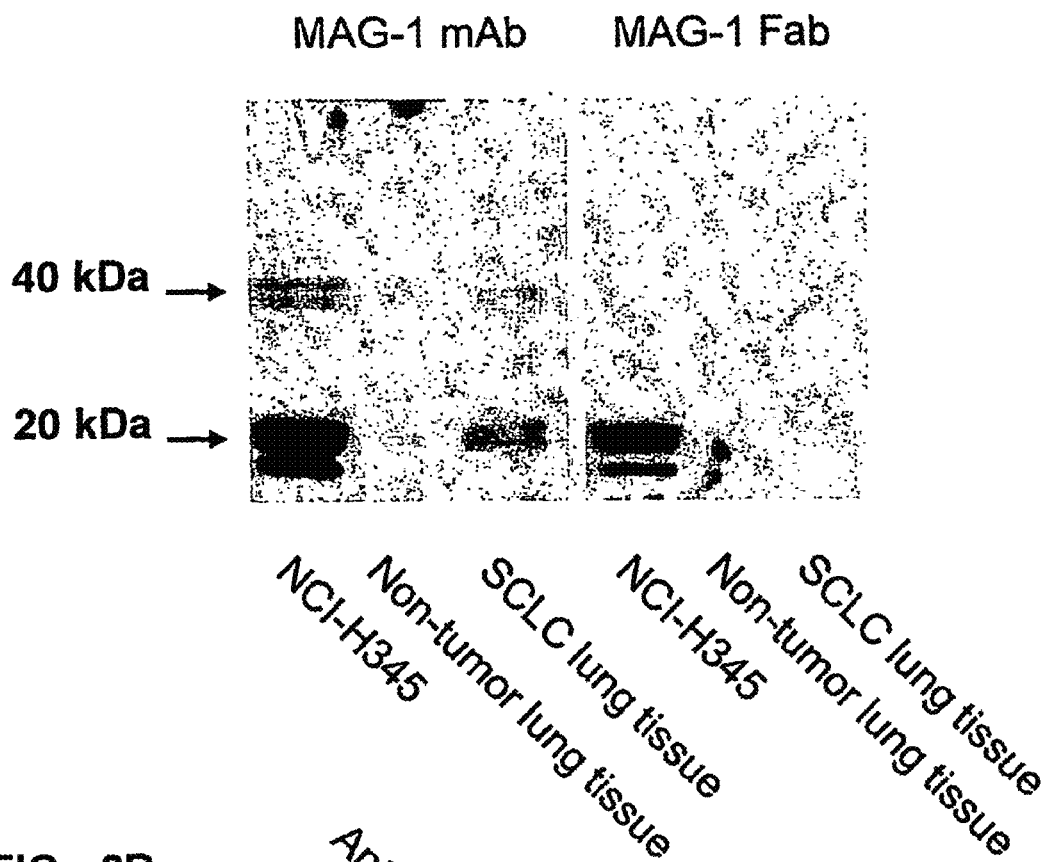
FIGS. 2A and 2B show detection of NRSA in cultured SCLC cells and human SCLC tissue by Western analysis.
Figure 2B:
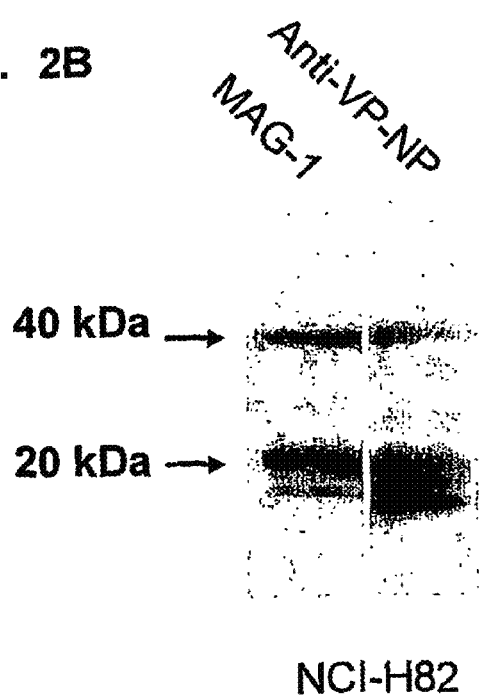

Only one product was detected in the reactions using RNA extracted from the SCLC tumor, SCLC cultured cells, and human hypothalamus tissue (FIG. 1). This band corresponds in size to that predicted (570 bp) for the VP message employing these particular amplification primers. There was no VP message detected in total RNA extract from the Beas-2B cells, while there was a faint band at ~570 bp detected in the non-tumor lung tissue extract. It is possible that this represents VP expression by small, undetected SCLC tumor cells embedded in the lung tissue sample, or expression by pulmonary neuroendocrine cells (Reynolds (2000) *Am. J. Physiol. Lung Cell. Mol. Physiol.* 278: L1256-L1263). However, when SDS-PAGE and Western analysis was performed using the MAG-1 mAb and Fab fragment, NRSA was detected in protein extracts from the cultured SCLC cells and tumor tissue, but not in protein extract from the non-tumor lung tissue (FIG. 2A). When cultured SCLC cell protein extract was examined using a polyclonal antibody raised against VP-NP (North, *Peptides* 14: 303-307, 1993), a banding pattern identical to that produced using the MAG-1 mAb was observed (FIG. 2B). The MAG-1 mAb and Fab, as well as the polyclonal anti-VP-NP antibody recognize proteins with molecular masses of ~20 and ~40 kDa, along with what appear to be degradation products and/or deglycosylated forms of the pro-VP protein. The ~20 kDa protein corresponds to the expected size for the pro-VP protein.

Similar techniques can be used to detect NRSA in other non-SCLC cancer tissues or samples.

EXAMPLE II

Detection of NRSA at the Surface of Cultured SCLC Cells

NCI-H82 cells were reacted with MAG-1 mAb or Fab, followed by FITC-labeled goat anti-mouse Fab-specific antibody, and fluorescence was measured on a FACStar apparatus (FIGS. 3A-3D). A similar level of staining was observed using a 1 µg/mL concentration of MAG-1 mAb or Fab, however the mean fluorescence measured was increased only ~2-fold when the concentration of Fab was used at 100 µg/ml, whereas it increased ~10-fold when using the mAb at that concentration. Since reactions were performed at 4° C. in the presence of sodium azide to inhibit internalization of proteins from the plasma membrane, these results indicate that the MAG-1 mAb has a higher binding capacity than MAG-1 Fab for NRSA on the surface of cultured SCLC cells. The mAb was also used to detect NRSA on the surface of Lu-165 and NCI-H345 cultured SCLC cells. The intensity of the fluorescence measured after staining with the isotype control mouse mAb was equivalent to that measured in unstained cells. The binding of the MAG-1 mAb to NRSA on the surface of cultured SCLC cells was also assessed by fluorescent microscopy. In all cases, a non-uniform pattern of staining of the cell surface was observed on SCLC cells while almost no staining was present when the isotype control antibody was used (FIGS. 4A-4C). Propidium iodide was used to stain the nuclei of the NCI-H82 cells for contrast, after the cells had been incubated with MAG-1, FITC -conjugated anti-mouse antibody, and fixed paraformaldehyde (FIG. 4A). When the NCI-H345 and Lu-165 cells were viewed by confocal microscopy, punctuate plasma membrane staining was observed (FIGS. 4B and 4C). While a quantitative assessment concerning the percentage of cells that were found to be immunoreactive with MAG-1 was not made, it is clear that there was a varied level of labeling of individual cells within the population of each cell type.

Similar techniques can be used to detect surface expression of NRSA in other non-SCLC cancer cells.

EXAMPLE III

Detection of NRSA on Human SCLC Tissue Sections

Figure 5A:
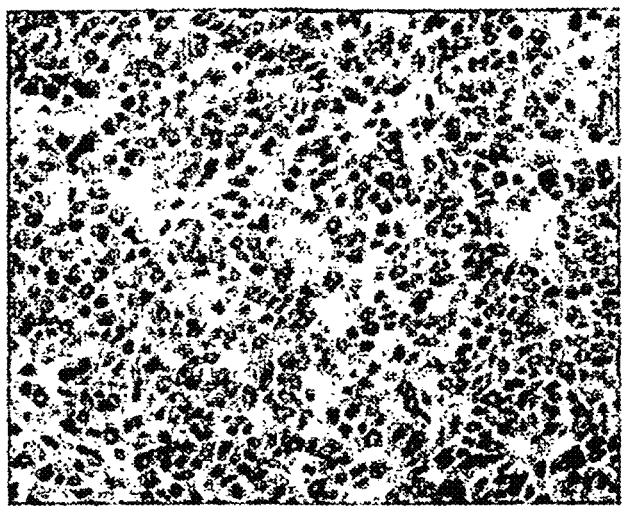
FIGS. 5A-5C illustrate immunohistochemical analysis of human tissue sections using MAG-1 mAb.
Figure 5B:
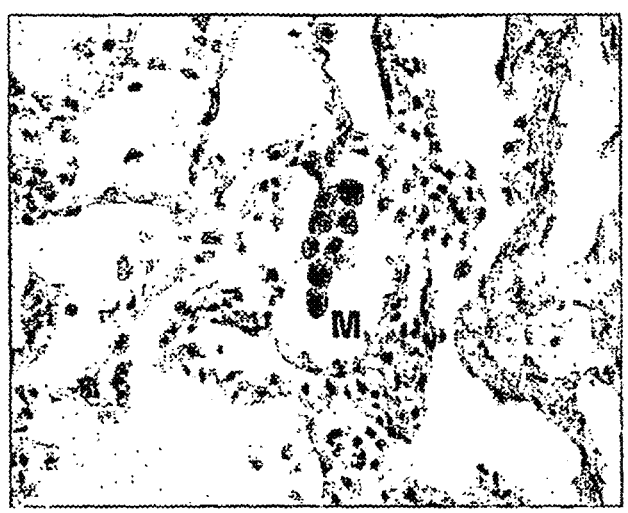
Figure 5C:
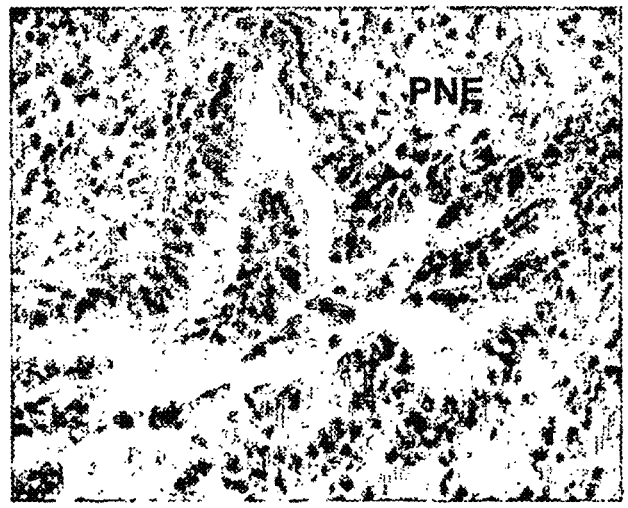

Human tissue sections were examined by immunohistochemical analysis using MAG-1, and staining was observed with small cell lung cancer (SCLC) tumor tissue (FIG. 5A), but not with normal lung tissue alveoli (FIG. 5B) or bronchioles (FIG. 5C). Both surface and intracellular staining are evident in the SCLC tumor section. Human hypothalamus was used as a positive control, however, only intracellular staining was observed on the hypothalamus tissue section (data not shown).

Similar techniques can be used to detect NRSA in other non-SCLC cancer tissue sections.

EXAMPLE IV

Figure 7:
FIG. 7 illustrates staining of human ductal carcinoma in situ (DCIS) tumor tissue sections examined by immunohistochemical analysis using MAG-1.
Figure 8:
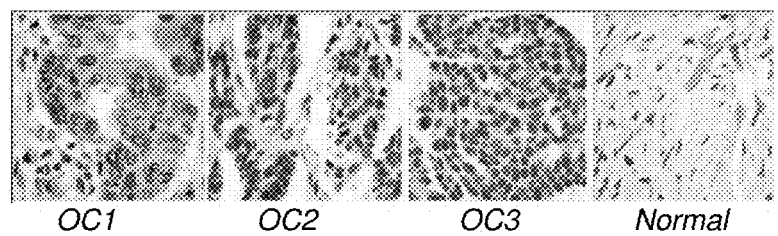
FIG. 8 shows representative immunohistochemistry (IHC) staining of three ovarian cancer sections (OC1, OC2, and OC3) with the mouse monoclonal antibody MAG-1.

Immunohistochemistry of Ductal Carcinoma In Situ and Aplastic Ductal Hyperplasia Tissue Sections Human tissue sections were examined by immunohistochemical analysis using MAG-1, and staining was observed with ductal carcinoma in situ (DCIS) tumor tissue (FIG. 7), but not with aplastic ductal hyperplasia (FIG. 8).
Confocal Microscopy
Exemplary Immunostaining Protocol for Confocal Microscopy
1. Plate cells inside ring on a coverslip (about 10,000 cells)
   1a. Place cells in 20-40 µL drop onto coverslip; let it sit for 10-20 minutes in incubator
   1b. Add complete media, 2 mL to cover all coverslip and return to incubator
2. Treat next day after about 24 hrs, with antibody MAG-1 at 10 µg/mL
3. For surface antigen-antibody staining, follow steps 4-10, then 19-23
4. Add antibody MAG-1 and incubate at 4° C. for about 4 hrs
5. Fix with Formalin 15 minutes at 4° C.
6. Wash cells twice with PBS with $Ca^{++}$, $Mg^{++}$
7. Add one drop of 0.5% NP40 for permeabilization. Incubate at 4° C. for 15 minutes.
8. Aspirate and add 1 drop of Phosphate Buffered Gelatin (PBG). Incubate at 4° C. for 5 min.
9. Wash 3 times with PBS with $Ca^{++}$, $Mg^{++}$
10. Add 20 uL of secondary antibody (rat anti-mouse FITC). Incubate at 4° C. for about 1 hr, under plastic cover on a slide tray with wetted paper towel to keep humidity high.
11. For internalization of antibody studies, follow steps 12-23
12. Add antibody MAG-1 and incubate at 37° C. (return to incubator) for about 4 hrs
13. Fix with Formalin 15 minutes at room temperature (RT)
14. Wash cells twice with PBS with $Ca^{++}$, $Mg^{++}$
15. Add one drop of 0.5% NP40 for permeabilization. Incubate at RT for 15 minutes
16. Aspirate and add 1 drop of Phosphate Buffered Gelatin (PBG). Incubate at RT for 5 min.
17. Wash 3 times with PBS with $Ca^{++}$, $Mg^{++}$
18. Add 20 µL of secondary antibody (rat anti-mouse FITC) at 1:2000 dilution. Incubate at RT for about 1 hr, under plastic cover on a slide tray with wetted paper towel to keep humidity high.
19. Wash 5 times with PBS with $Ca^{++}$, $Mg^{++}$
20. If staining with DAPI, add 20 µL of 0.7, 1.4, 2.8 or 5.7 µM DAPI. Incubate at RT for 5 min.
    (CFP slides should have DAPI at only 0.7 µM)
21. Aspirate, then add 1 drop of Formalin. Incubate at RT for 5 min Postfixed with Formalin.
22. Wash twice with PBS with $Ca^{++}$, $Mg^{++}$
23. Mount coverslip on slide

EXAMPLE V

Immunohistochemistry (IHC) of Non-SCLC and Non-Breast Cancers

The examples above demonstrate that MAG-1 can detect abnormal provasopressin expression on SCLC and breast cancer cells. This example provides evidence that abnormal provasopressin expression is also identified in virtually all cancer tissues examined, especially in tissues from ovarian cancer, prostate cancer, and neuroendocrine cancer.

The sABC technique of IHC using MAG-1, with citrate "antigen recovery," on 4 µm sections was employed (SSI System, Biogenex). Controls included successfully blocking primary antibody with excess peptide antigen. These studies revealed the presence of GRSA in seemingly all neoplastic cells of all tumor tissue sections.

Specifically, Applicants have so-far performed IHC on 22 cases of invasive ovarian cancer represented by tissue arrays and tissue sections. These studies revealed a positive staining with MAG-1, and therefore the presence of GRSA in seemingly all neoplastic cells of all tumor tissue sections. In contrast, no staining was found with samples from normal human ovary, kidney, breast, liver, lung, and 28 other normal human tissues. See FIG. 8, showing a representative IHC staining result with MAG-1 on sections of three ovarian cancers (OC1, OC2, and OC3).

Table 2 below provides a list of cancers tested positive for provasopressin overexpression.

TABLE 2

| List of Cancers Expressing Provasopressin | |
|---|---|
| Cancer Type | Positive Tumors |
| Brain | + |
| Breast | + |
| Colon | + |
| Endometrial | + |
| Gastric | + |

TABLE 2-continued

List of Cancers Expressing Provasopressin

| Cancer Type | Positive Tumors |
|---|---|
| Ovarian | + |
| Pancreatic | + |
| Prostate | \+ |
| Rectum | + |
| Testicular | + |

Figure 9:
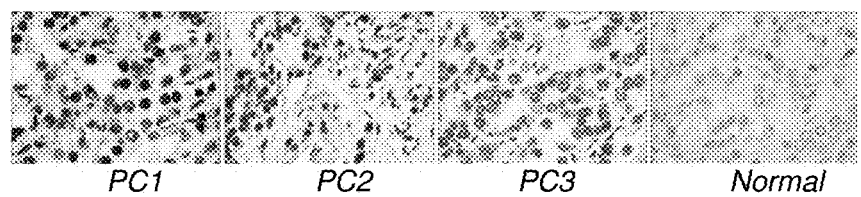
FIG. 9 shows representative immunohistochemistry (IHC) staining of three prostate cancer sections (PC1, PC2, and PC3) with the mouse monoclonal antibody MAG-1.

Applicants have also performed IHC on 22 cases of prostate cancer represented by tissue arrays and tissue sections. As with ovarian cancer, these prostate cancer samples all gave positive IHC staining with MAG-1, showing the common expression of the GRSA surface marker by these tumors. Again, in contrast, there was no observed reaction of MAG-1 with normal prostate tissues (FIG. 9).

In all cases with ovarian cancer and prostate cancer samples, no staining by MAG-1 was observed in the presence of an excess of a competing peptide antigen C-18 VAG (a component of GRSA). This result demonstrates the specificity of the MAG-1 antibody for GRSA.

EXAMPLE VI

GRSA is Present on the Surface of Ovarian Cancer Cell Lines

This experiment demonstrates that the provasopressin antigen GRSA is present on the surface of ovarian cancer cell lines.

Three ovarian cancer cell lines were tested in this example: A2780, A2008, and SK-OV3 cells. Cell surface expression of GRSA was demonstrated both by Western analysis and by confocal microscopy employing MAG-1 (see below).

Figure 10:
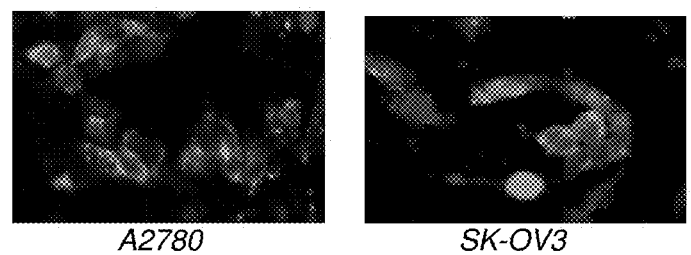
FIG. 10 shows confocal images of A2780 and SK-OV3 ovarian cancer cells stained with fluorescent labeled MAG-1 antibody.

It was also found that interaction between GRSA and MAG-1 on these cells resulted in an internalization of the antibody-antigen complex. FIG. 10 shows confocal image of surface fluorescent staining of GRSA on ovarian cancer cells A2780 and SK-OV3.

Also see FIGS. 13A-13E for confocal images showing cell surface localization of the GRSA antigen in ovarian cancer cell lines SKOV3 and OV2008.

EXAMPLE VII

GRSA is Present on the Surface of Prostate Cancer Cell Lines

This experiment demonstrates that the provasopressin antigen GRSA is present on the surface of prostate cancer cell lines.

Two prostate cancer cell lines were tested in this example: LNCAP cells and PC3 cells. Again, cell surface expression of GRSA was demonstrated both by Western analysis and by confocal microscopy employing MAG-1 (see below).

Figure 11:
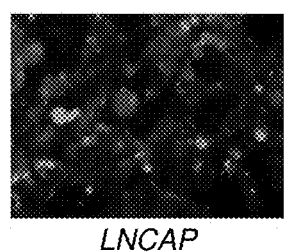
FIG. 11 shows confocal images of LNCAP lung cancer cells stained with fluorescent labeled MAG-1 antibody.

It was also found that interaction between GRSA and MAG-1 on these cells resulted in an internalization of the antibody-antigen complex. FIG. 11 shows confocal image of surface fluorescent staining of GRSA on LNCAP prostate cancer cells.

Also see FIGS. 13A-13E for confocal images showing cell surface localization of the GRSA antigen in prostate cancer cell line PC3.

FIGS. 13A-13E further show the same cell surface localization for the GRSA antigen in pancreatic cancer cell lines bxpc3 and panc1.

EXAMPLE VIII

MAG-1 Inhibits Breast Cancer and Ovarian Cancer Growth In Vivo

This experiment demonstrates that the anti-provasopressin antibody MAG-1 inhibits cancer growth in vivo in nude mice experiments.

Figure 12A:
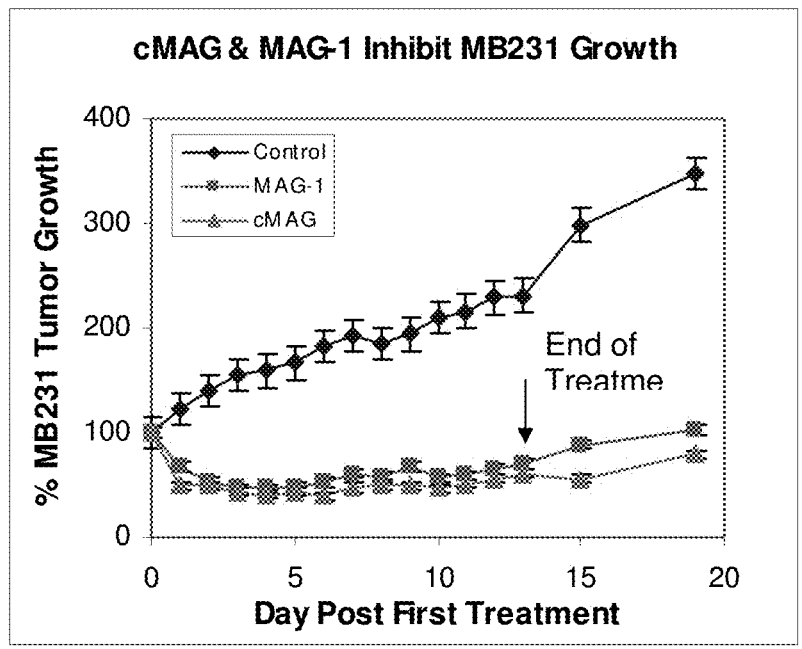
FIGS. 12A and 12B show that cMAG and MAG-1 inhibit MB231 breast cancer cell line growth, and that MAG-1 inhibits A2780 ovarian cancer cell line growth.
Figure 12B:
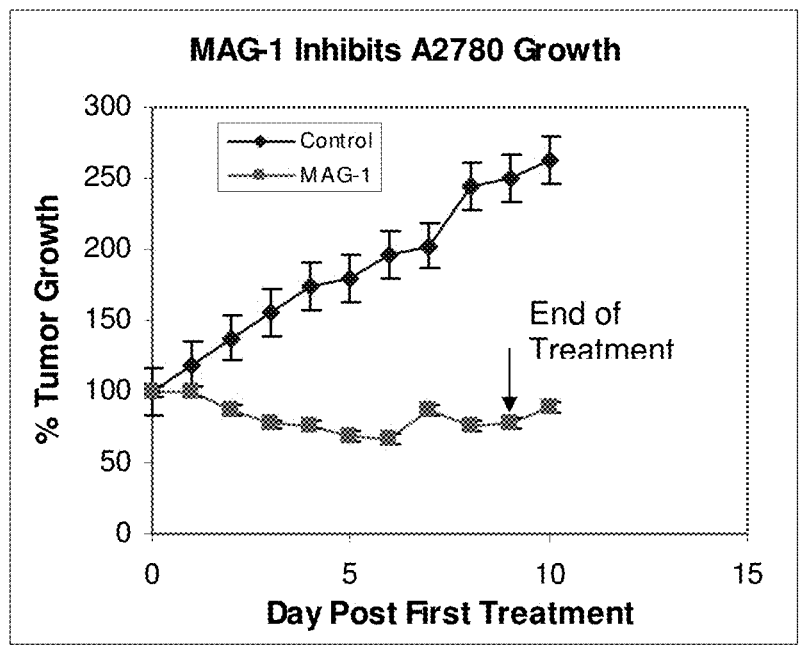

See FIGS. 12A and 12B.

The above findings, together with filed findings for breast cancer and small-cell lung cancer, demonstrate that MAG-1 antibody and other agents that target the GRSA surface antigen can be used for the identification/diagnosis/treatment of tumors in provasopressin-expressing cancer cells, such as ovarian, prostate, and endometrial tissues. These agents can serve, either in their natural form or in their modified forms, or in combination with radiation or chemotherapeutics, as targeting therapeutic agents for these disease states.

EXAMPLE IX

Generation of Chimeric (cMAG-1) and Humanized (hMAG-1) Forms of MAG-1 Antibodies Cloning of MAG-1 Heavy and Light Chain Using universal primers, Applicants have successfully cloned the complete heavy and light chain sequences of the mouse MAG-1 antibody. The DNA sequences are consistent with the variable region of the heavy and light chains Applicants cloned previously.

The amino acid sequences of the heavy and light chains of the mature protein, at the amino terminal regions, were determined by protein sequencing after isolating the reduced and s-alkylated heavy and light chains by SDS polyacrylamide gel electrophoresis. The amino terminal regions of the heavy and light chains obtained by protein sequencing are summarized below.

N-terminal amino acid sequence:

```
(i) Heavy Chain:
EVKLEGSGGGG (ii) Light Chain:
DVVMTQTPLSLS
```

These sequences are consistent with the amino acid sequences at the amino terminals coded by the cloned DNA.

Construction of Chimeric and Humanized MAG-1

(a) Construction and Expression of Chimeric MAG-1 (cMAG-1)

Based on the DNA sequences of the cloned mouse MAG-1 heavy and light chains, Applicants searched GenBank and identified human antibody constant regions, which have about 73-78% homology with the mouse MAG-1 constant regions. Using these sequences, Applicants prepared and expressed a few human-mouse chimeric antibody constructs using a CMV1 promoter in Chinese Hamster Ovary (CHO) cells as well as in HEK 293 cells by transient expression. Applicants then selected a CHO clone 2L-Neo1-MTX50 for further analysis. This clones produced about 5 µg/10⁶ cells per day. Using antigen-affinity chromatography, Applicants obtained cMAG-1 thus produced for further analysis.

(b) Construction and Expression of Humanized MAG-1 (hMAG-1)

Applicants first identified several human framework regions which have at least 70% homology with the mouse framework regions of MAG-1. Applicants then designed three sets of heavy and light chain variable regions based on the human framework sequences and certain amino acid substitutions using computer modeling. Applicants screened all the expressed constructs, then selected and produced a sufficient quantities of a H2L2 (hMAG-1) construct by transient expression in HEK 293 cells for further analysis. The hMAG-1 antibody was purified using Protein A affinity chromatography.

Analysis of Chimeric MAG-1 and Humanized MAG-1—Dissociation Constants

Based on competitive inhibition of $^{125}$I antigen binding, it has been observed that the dissociation constants of the chimeric antibody cMAG-1 and the mouse antibody MAG-1 are essentially the same, while the dissociation constant for the humanized MAG (hMAG-1) is about 10 folds higher compared to cMAG-1 and MAG-1 (see Table 1).

TABLE 1

Dissociation Constants of mouse, chimeric and humanized MAG-1

| Antibody | Dissociation Constant |
| --- | --- |
| Mouse MAG-1 | $5.0 \times 10^{-9}$M |
| Chimeric MAG-1 | $5.7 \times 10^{-9}$M |
| Humanized MAG-1 | $5.3 \times 10^{-8}$M |

Binding of Antibody to Surface Antigen of Tumor Cells by Confocal Microscopy

Figures 14A, 14B, 14C:
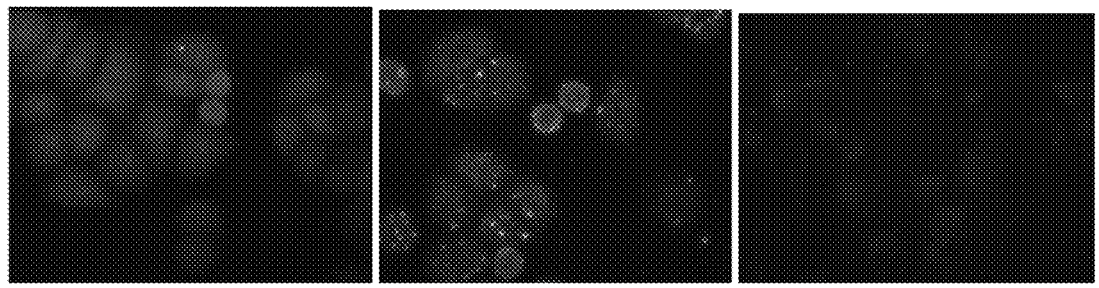
FIGS. 14A-14C show confocal microscopy images of SKBr3 cells incubated with (FIG. 14A) mouse antibody MAG-1, (FIG. 14B) chimeric antibody cMAG-1, and (FIG. 14C) humanized antibody hMAG-1.

Using confocal microscopy, Applicants tested the ability of both chimeric and humanized MAG-1 antibodies to bind to the cell surfaces of breast cancer cell lines. In spite of its relatively lower binding affinity, humanized MAG-1 was shown to bind to the breast cancer cells, so did the chimeric and mouse antibodies (FIGS. 14A-14C).

Animal Studies

Applicants compared the ability of the chimeric antibody cMAG-1 and the mouse antibody MAG-1 to inhibit the growth of estrogen-dependent MCF-7 and estrogen independent (triple negative) MDA-MB231 xenografts in nu/nu mice.

Figure 15A:
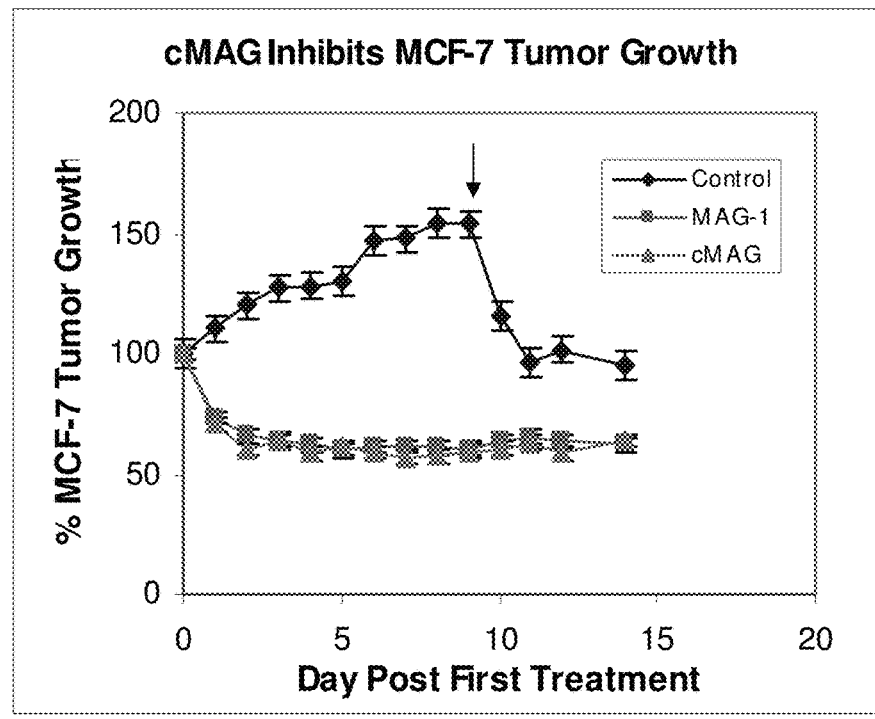
FIGS. 15A and 15B show results of treating MCF-7 tumors (FIG. 15A) and MDA-MB231 tumors (FIG. 15B) in nu/nu mice with cMAG-1 and mMAG-1. The arrow indicates the date mMAG-1 was injected in the control group mice.

Three groups of nu/nu mice (8 mice for each group) were injected with $1 \times 10^7$ MCF-1 or MDA-MB231 tumor cells per mouse s.c. on the right flank, and the tumors were allowed to grow to an average of about 300 mm³ in about 30 days. For MCF-7 cells, prior to tumor cell injection, an estrogen pellet was inserted below the skin on the back just below the neck. At Day 0 of the treatment, 50 µg of cMAG-1 or mMAG-1 antibody in PBS solution was injected intraperitoneally, once per day for 14 days. The control group was injected similarly, but with ×PBS. Tumor volume was measured daily, and the relative average sizes of the tumors in each group, as compared to the volume at Day 0, were plotted against a time course of treatment in FIGS. 15 A & 15B. In FIG. 15A, at treatment Day 10, the control group was injected with mMAG-1, as shown by the arrow.

Figure 15B:
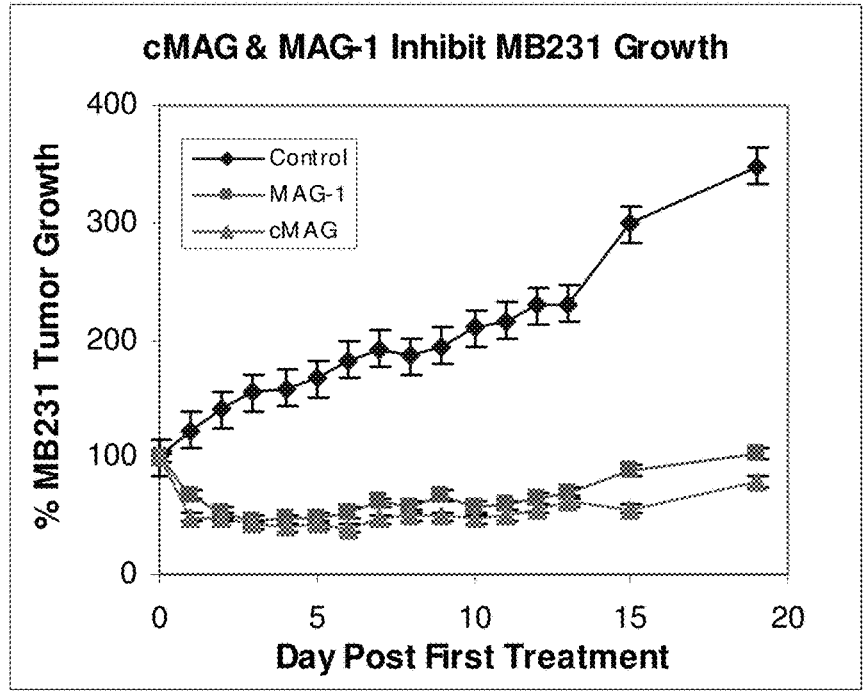

The data shows that, in both instances, cMAG-1 was as efficacious as mouse MAG-1 in terms of inhibiting tumor growth or shrinking tumor size during treatment (FIGS. 15A & 15B). After 2 days of daily injections of cMAG-1 and mMAG-1, the size of the injected tumors shrank to about 60% of that of the original tumors on Day 0 (Day of commencing treatment), and tumor sizes remained stable for the remaining treatment period. FIG. 15B further shows that, in the control group, after the average tumor size has reached about 150% of the original size at Day 10, a single injection of mMAG-1 dramatically reduced average tumor size to about the original size (100%).

Mechanism of Action-Internalization of Mouse and Chimeric Antibody

In this experiment, Applicants investigated whether the antibody-antigen complex is internalized, by allowing the MAG-1 antibody to bind to the surface of the SKBr3 cells at 4° C. and 37° C., respectively, for about 24 hr before analyzing the presence of antibodies inside the cells.

As show in the confocal microscopy images in FIG. 16A, MAG-1 was detected inside the cells incubated at 37° C., but not inside cells incubated at 4° C., indicating that the antibody-antigen complex was internalized. Monoclonal antibody 520C9 (FIG. 16B), which binds to the Herb2 receptor on the SKBr3 cells, was used as a positive control.

Similarly, Applicants have shown that chimeric antibody cMAG-1 was also internalized after incubation with the SKBr3 cells for 24 hrs at 37° C.

EXAMPLE X

Synergistic Efficacy of MAG-1 with Chemotherapy in the Treatment of SCLC

In this example, Applicants have demonstrated that MAG-1 enhances the efficacy of cyclophosphamide in combination therapy.

Specifically, the animals were treated as in Example IX with about 100 µg of MAG-1 daily for 11 days, subsequent to treatment with about 50 mg/kg b.w. of cyclophosphamide daily for 3 days. Three groups of nu/nu mice (8 animal per group) were injected with $1 \times 10^7$ recurrent H82 SCLC cells per mouse s.c. on the right flank, and the tumors were allowed to grow to an average of about 300 mm³ in about 14 days. All treatment was carried out by injection intraperitoneally. The control group animals were injected with PBS daily for 14 days, the cyclophosphamide group was injected with 50 mg/kg of cylcophosphamide per animal daily for 3 days, while the combined therapy group was treated with 50 mg/kg of cyclophosphamide per animals daily for 3 days and thereafter with 100 µg of MAG-1 per animal daily for another 11 days. The data in FIG. 17 shows synergistic efficacy between MAG-1 and cyclophosphamide in treating SCLC xenografts.

It will be apparent to those skilled in the art that various modifications and variations can be made in the present invention without departing from the scope or spirit of the invention. Other embodiments of the invention will be apparent to those skilled in the art form consideration of the specification and practice of the invention disclosed herein. It is intended that the specification and examples be considered as exemplary only, with the true scope and spirit of the invention being indicated by the following claims.

POLYPEPTIDE SEQUENCES
SEQ ID NO: 1:
Ala-Pro-Glu-Pro-Phe-Glu-Pro-Ala

SEQ ID NO: 4:
GGSSRSS

-continued

SEQ ID NO: 5:
Val-Gln-Leu-Ala-Gly-Ala-Pro-Glu-Pro-Phe-Glu-Pro-
Ala-Gln-Pro-Asp-Ala-Tyr

SEQ ID NO: 6:
Val-Gln-Leu-Ala-Gly-Ala-Pro-Glu-Pro-Phe

SEQ ID NO: 7:
GSTSG

We claim:

1. A method of treating a provasopressin-expressing (pro-VP-expressing) cancer, comprising administering, to a patient in need thereof, a therapeutically effective amount of a provasopressin-binding antibody or an antigen-binding portion thereof specific for the C-terminal 18-amino-acid VAG region of provasopressin (pro-VP), wherein the pro-vasopressin-binding antibody is MAG-1, a humanized antibody thereof, or a chimeric antibody thereof, and wherein the cancer is a neuroendocrine cancer or a pancreatic cancer.

2. The method of claim 1, wherein the neuroendocrine cancer is a brain, gastroenteric, ovarian, endomedrial, testicular, adrenal, or skin cancer.

3. The method of claim 1, wherein the antigen-binding portion thereof is scFv, Fab, F(ab')$_2$, Fd, Fv, or dAb.

4. The method of claim 1, further comprising administering an effective amount of a pharmaceutical composition comprising a chemotherapeutic agent.

5. The method of claim 4, wherein the pharmaceutical composition comprising a chemotherapeutic agent further comprises epinephrine.

6. The method of claim 4, wherein the pharmaceutical compositions are administered in a single formulation.

7. The method of claim 1, further comprising administering an effective amount of a pharmaceutical composition comprising at least one of dexamethasone, IBMX, 8-bromoadenosine 3',5'-cyclic monophosphate (8br-cAMP), cyclophosphamide, cisplatin, etoposide VP-16, and forskolin.

8. The method of claim 1, further comprising performing surgical removal of at least one tumor from the patient.

9. The method of claim 1, further comprising performing radiation therapy.

10. The method of claim 1, further comprising administering a somatostatin or an analogue thereof.

11. The method of claim 1, further comprising administering at least one of imatinib, sunitinib, temozolide, thalidomide, sorafenib, and panitumumab.

12. The method of claim 1, wherein the antibody or antibody-binding portion thereof comprises a label.

13. The method of claim 12, wherein the label is selected from the group consisting of a fluorescent label, a radiolabel, a toxin, a metal compound, and biotin.

14. The method of claim 13, wherein the fluorescent label is selected from the group consisting of Texas Red, phycoerythrin (PE), cytochrome c, and fluorescent isothiocyanate (FITC).

15. The method of claim 13, wherein the radiolabel is selected from the group of $^{32}$P, $^{33}$P, $^{43}$K, $^{47}$Sc, $^{52}$Fe, $^{57}$Co, $^{64}$Cu, $^{67}$Ga, $^{67}$Cu, $^{68}$Ga, $^{71}$Ge, $^{75}$Br, $^{76}$Br, $^{77}$Br, $^{77}$As, $^{77}$Br, $^{81}$Rb/$^{81M}$Kr, $^{87M}$Sr, $^{90}$Y, $^{97}$Ru, $^{99}$Tc, $^{100}$Pd, $^{101}$Rh, $^{103}$Pb, $^{105}$Rh, $^{109}$Pd, $^{111}$Ag, $^{111}$In, $^{113}$In, $^{119}$Sb, $^{121}$Sn, $^{123}$I, $^{125}$I, $^{127}$Cs, $^{128}$Ba, $^{129}$Cs, $^{131}$I, $^{131}$Cs, $^{143}$Pr, $^{153}$Sm, $^{161}$Tb, $^{166}$Ho, $^{169}$Eu, $^{177}$Lu, $^{186}$Re, $^{188}$Re, $^{189}$Re, $^{191}$Os, $^{193}$Pt, $^{194}$Ir, $^{197}$Hg, $^{199}$Au, $^{203}$Pb, $^{211}$At, $^{212}$Bi and $^{213}$Bi.

16. The method of claim 13, wherein the toxin is selected from the group consisting of ricin, ricin A chain (ricin toxin), *Pseudomonas* exotoxin (PE), diphtheria toxin (DT), *Clostridium perfringens* phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin.

17. A method of killing or inhibiting the growth of a provasopressin-expressing cancer cell, comprising contacting the provasopressin-expressing cancer cell with a provasopressin-binding antibody or an antigen-binding portion thereof specific for the C-terminal 18-amino-acid VAG region of provasopressin (pro-VP), wherein the provasopressin-binding antibody is MAG-1, a humanized antibody thereof, or a chimeric antibody thereof, and wherein the provasopressin-expressing cancer cell is from a neuroendocrine cancer or a pancreatic cancer.

18. The method of claim 17, further comprising contacting the provasopres sin-expressing cancer cell with a chemotherapeutic agent.

* * * * *